(12) United States Patent
Smith et al.

(10) Patent No.: US 10,790,046 B2
(45) Date of Patent: Sep. 29, 2020

(54) SYSTEMS, METHODS, AND APPARATUS FOR DRAWING AND EDITING CHEMICAL STRUCTURES ON A USER INTERFACE VIA USER GESTURES

(71) Applicant: PerkinElmer Informatics, Inc., Waltham, MA (US)

(72) Inventors: Robin Young Smith, Boston, MA (US); Scott Gregory Flicker, Raleigh, NC (US); Daniel Malcolm Oberlin, Bedford, MA (US); Andrew Smellie, Candia, NH (US)

(73) Assignee: PerkinElmer Informatics, Inc., Waltham, MA (US)

( * ) Notice: Subject to any disclaimer, the term of this patent is extended or adjusted under 35 U.S.C. 154(b) by 262 days.

(21) Appl. No.: 15/944,642

(22) Filed: Apr. 3, 2018

(65) Prior Publication Data
US 2018/0349566 A1 Dec. 6, 2018

Related U.S. Application Data

(62) Division of application No. 13/404,671, filed on Feb. 24, 2012, now Pat. No. 9,977,876.

(51) Int. Cl.
*G06F 3/0488* (2013.01)
*G16C 20/80* (2019.01)

(52) U.S. Cl.
CPC ......... *G16C 20/80* (2019.02); *G06F 3/04883* (2013.01)

(58) Field of Classification Search
None
See application file for complete search history.

(56) References Cited

U.S. PATENT DOCUMENTS

| | | |
|---|---|---|
| 4,967,372 A | 10/1990 | Feldman |
| 5,008,831 A | 4/1991 | Feldman |

(Continued)

FOREIGN PATENT DOCUMENTS

| | | |
|---|---|---|
| CN | 102165394 A | 8/2011 |
| EP | 1526471 A1 | 4/2005 |

(Continued)

OTHER PUBLICATIONS

Brooks et al., "Project GROPE—HapticDisplays for Scientific Visualization", SIGGRAPH '90, Computer Graphics, v. 24, n. 4, p. 177-185, Aug. 1990. (Year: 1990).*

(Continued)

*Primary Examiner* — Jennifer N To
*Assistant Examiner* — Joseph R. Burwell
(74) *Attorney, Agent, or Firm* — Banner & Witcoff, Ltd.

(57) ABSTRACT

Systems, methods, and apparatus are provided that allow a user to draw and edit a chemical structure using one or more gestures performed on an input interface, such as a touch pad or touch screen. For example, the user may assign an atom label to a chemical structure representation by performing a press and tap gesture, change a chemical bond characteristic in the chemical structure representation by performing a tap gesture, and/or lengthen a molecular chain in the chemical structure representation by performing a drag gesture. The user may also rotate the chemical structure representation in the graphical display by performing one or more rotation gestures.

18 Claims, 11 Drawing Sheets

(56) References Cited

U.S. PATENT DOCUMENTS

| | | |
|---|---|---|
| 5,249,137 A | 9/1993 | Wilson et al. |
| 5,386,507 A | 1/1995 | Teig et al. |
| 5,461,580 A | 10/1995 | Facci et al. |
| 6,017,390 A | 1/2000 | Charych et al. |
| 6,304,869 B1 | 10/2001 | Moore et al. |
| 6,434,490 B1 | 8/2002 | Agrafiotis et al. |
| 6,582,233 B1 | 6/2003 | Clark |
| 7,043,415 B1 | 5/2006 | Dunlavey et al. |
| 7,138,997 B2 | 11/2006 | Balakrishnan et al. |
| 7,613,574 B2 | 11/2009 | Verseput |
| 7,663,607 B2 | 2/2010 | Hotelling et al. |
| 7,705,830 B2 | 4/2010 | Westerman et al. |
| 7,912,689 B1 | 3/2011 | Helson |
| 8,296,670 B2 | 10/2012 | Matthews et al. |
| 8,407,578 B2 | 3/2013 | Boyer et al. |
| 8,479,122 B2 | 7/2013 | Hotelling et al. |
| 2002/0049548 A1 | 4/2002 | Bunin |
| 2002/0051999 A1 | 5/2002 | Sepetov et al. |
| 2002/0107359 A1 | 8/2002 | Hogarth et al. |
| 2003/0194687 A1 | 10/2003 | Clark |
| 2003/0220776 A1* | 11/2003 | Phillips .................. F17C 11/005 703/11 |
| 2004/0003000 A1 | 1/2004 | Smith et al. |
| 2004/0024493 A1 | 2/2004 | Fagrell et al. |
| 2004/0088118 A1 | 5/2004 | Jensen et al. |
| 2004/0122641 A1 | 6/2004 | Miller et al. |
| 2004/0171062 A1 | 9/2004 | Hirth et al. |
| 2005/0094205 A1 | 5/2005 | Lo et al. |
| 2005/0123993 A1 | 6/2005 | Brunner et al. |
| 2005/0131894 A1 | 6/2005 | Vuong |
| 2005/0177280 A1 | 8/2005 | Almstetter et al. |
| 2006/0026521 A1 | 2/2006 | Hotelling et al. |
| 2006/0040322 A1 | 2/2006 | Archetti et al. |
| 2006/0061595 A1 | 3/2006 | Goede et al. |
| 2006/0277201 A1 | 12/2006 | Dorsett |
| 2007/0177803 A1 | 8/2007 | Elias et al. |
| 2007/0192747 A1 | 8/2007 | Phelan et al. |
| 2007/0198561 A1* | 8/2007 | Lee ........................ G06F 3/0483 |
| 2007/0276636 A1 | 11/2007 | Wythoff |
| 2008/0036743 A1 | 2/2008 | Westerman et al. |
| 2008/0136785 A1 | 6/2008 | Baudisch et al. |
| 2008/0165140 A1 | 7/2008 | Christie et al. |
| 2008/0213663 A1 | 9/2008 | Hu et al. |
| 2008/0309632 A1 | 12/2008 | Westerman et al. |
| 2009/0058820 A1* | 3/2009 | Hinckley ............ G06F 3/04883 345/173 |
| 2009/0063427 A1 | 3/2009 | Zuta et al. |
| 2009/0079700 A1 | 3/2009 | Abernathy |
| 2009/0177455 A1* | 7/2009 | Banerjee .................. G06T 13/20 703/12 |
| 2009/0273571 A1 | 11/2009 | Bowens |
| 2009/0278806 A1 | 11/2009 | Duarte et al. |
| 2009/0288044 A1 | 11/2009 | Matthews et al. |
| 2010/0060588 A1 | 3/2010 | Fong |
| 2010/0079369 A1 | 4/2010 | Hartmann et al. |
| 2011/0041098 A1 | 2/2011 | Kajiya et al. |
| 2011/0055696 A1 | 3/2011 | Dollar et al. |
| 2011/0072339 A1 | 3/2011 | Boyer et al. |
| 2011/0276589 A1 | 11/2011 | Smith et al. |
| 2012/0078853 A1 | 3/2012 | Huang et al. |
| 2012/0144293 A1* | 6/2012 | Kim .................... G06F 3/04817 715/255 |
| 2012/0154440 A1 | 6/2012 | Nicholls et al. |
| 2012/0185513 A1 | 7/2012 | Samukawa |
| 2012/0317521 A1* | 12/2012 | Ludwig ................ G06F 40/268 715/863 |
| 2013/0061163 A1 | 3/2013 | Clark et al. |
| 2013/0069860 A1* | 3/2013 | Davidson .............. G06F 3/0488 345/156 |
| 2014/0089329 A1 | 3/2014 | Kozloski et al. |
| 2014/0173475 A1* | 6/2014 | Smellie .................. G16C 20/80 715/765 |
| 2014/0267240 A1 | 9/2014 | Smith |
| 2014/0282106 A1 | 9/2014 | Smith et al. |
| 2014/0337725 A1 | 11/2014 | Smith et al. |
| 2015/0112604 A1 | 4/2015 | Smith |
| 2015/0199797 A1 | 7/2015 | Palo |
| 2017/0351846 A1* | 12/2017 | Clark .................... H01L 23/522 |

FOREIGN PATENT DOCUMENTS

| | | |
|---|---|---|
| EP | 2567338 A1 | 3/2013 |
| GB | 2493830 A | 2/2013 |
| WO | 2007092842 A2 | 8/2007 |
| WO | 2011140148 A1 | 11/2011 |
| WO | 2013126077 A1 | 8/2013 |

OTHER PUBLICATIONS

Bryfczynski, "Organic Pad: A Tablet PC Based Chemistry Tool", Proceedings of the 46th Annual Southeast Regional Conference on XX (ACM-SE 46), pp. 162-165, 2008. (Year: 2008).*

"ChemDoodle Review", https://www.macinchem.org/reviews/chemdoodle-review.php, 2011. (Year: 2011).*

Cooper et al., "OrganicPad: an interactive freehand drawing application for drawing Lewis structures and the development of skills in organic chemistry", Chem. Educ. Res. Pract., v. 10, pp. 296-301, 2009. (Year: 2009).*

Ertl, "Molecular structure input on the web", Journal of Cheminformatics, 2:1, 2010. (Year: 2010).*

Kim et al., "A Gesture-Based Molecular Modeling System", ICAT 2004. (Year: 2004).*

Logtenberg, "Designing interaction with molecule visualizations on a multi-touch table", Research for Capita Selecta, a Twente University course. Enschede, The Netherlands: Twente University, 2008. (Year: 2008).*

Maier et al., "What Do You Do When Two Hands Are Not Enough? Interactive Selection of Bonds Between Pairs of Tangible Molecules", IEEE Symposium on 3D User Interfaces, pp. 83-90, 2010. (Year: 2010).*

O'Hagan et al., "Visual Gesture Interfaces for Virtual Environments", Interacting with Computers, v. 14, pp. 231-250, 2002. (Year: 2002).*

Pargas et al., "OrganicPad: A Tablet PC Based Interactivity Tool for Organic Chemistry," First International Workshop on Pen-Based Learning Technologies (PLT 2007), pp. 1-6, 2007. (Year: 2007).*

Park et al., "A Molecular Modeling System Based on Dynamic Gestures", International Conference on Computational Science and Its Applications (ICCSA 2005), pp. 886-895, 2005. (Year: 2005).*

Pavlovic et al., "Gestural interface to a visual computing environment for molecular biologists," Proceedings of the Second International Conference on Automatic Face and Gesture Recognition, pp. 30-35, 1996. (Year: 1996).*

Prins et al., "A Virtual Environment for Steered Molecular Dynamics", Future Generation Computer Systems, v. 15, pp. 1-12, 1999. (Year: 1999).*

Sharma et al., "Speech/gesture interface to a visual computing environment for molecular biologists", Proceedings of 13th International Conference on Pattern Recognition, pp. 964-968, 1996. (Year: 1996).*

Sharma et al., "Speech/Gesture Interface to a Visual-Computing Environment", IEEE Computer Graphics and Applications, pp. 29-37, Mar. 2000. (Year: 2000).*

Zeller et al., "A visual computing environment for very large scale biomolecular modeling," Proceedings IEEE International Conference on Application-Specific Systems, Architectures and Processors, pp. 3-12, 1997. (Year: 1997).*

Dec. 20, 2018—(AU) Office Action—App 2018204023.
Oct. 25, 2018—(EP) Examination Report—App 12716771.6.
Nov. 6, 2018—(AU) Office Action—App 2018204023.
Jun. 19, 2019—(AU) Office Action—AU 2018204023.
Jun. 6, 2019—(CA) Office Action—App 2,865,004.
Oct. 8, 2019—(EP) Office Action—App 12716771.6.
Jun. 12, 2018—(CA) Office Action—App 2,865,004.
Carmigniani, J. et al., "Augmented Reality Technologies, Systems and Applications", Multimedia Tools and Applications" 51: pp. 341-377 (2011).

(56) References Cited

OTHER PUBLICATIONS

Clark A.M., "Basic Primitives for Molecular Diagram Sketching" Journal of Cheminformatics 2: 8 (2010).
Apr. 9, 2014—(EP) European Search Report—App 13275308.8.
Aug. 13, 2014—(EP) European Search Report—App 13275308.8.
Furlon, Rod "Build Your Own Google Glass, Resources Hands On" IEEE Spectrum, IEEE Inc., vol. 50, No. 1, pp. 20-21, Jan. 1, 2013.
Guidice N.A. et al., "Learning Non-Visual Graphical Information Using a Touch-Based Vibro-Audio Interface" Proceedings of the 14th International ACM Sigaccess Conference on Computers and Accessibility, Assets '12, 103-110, Jan. 1, 2012.
Aug. 13, 2014—(WO) International Search Report and Written Opinion—App PCT/US2014/016249.
Aug. 4, 2014—(WO) International Search Report and Written Opinion—App PCT/US2014/035685.
Li et al., "Personal Experience with Four Kinds of Chemical Structure Drawing Software" Review on ChemDraw, ChemWindow, ISIS/Draw, and ChemSketch, J. Chem. Inf. Comput. Sc. 44:1886-1890 (2004).
Shine et al., "ChemPad3 a tutorial" May 21, 2008, 10 pages.
Toennies J.L. et al., "Toward Haptic/Aural Touchscreen Display of Graphical Mathtematics for the Education of Blind Students" WHC, IEEE, 373:378 (2011).
Australian Patent Application No. 2011248243, APO Examination Report No. 1, dated Nov. 5, 2013, 3 pages.
Bennett Samsun's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.
May 29, 2013—(CN) Office Action—App 201190000597.X.
Gonzalez-Villanueva et al. "WallShare: A Collaborative Multi-Pointer System for Portable Devices" Nov. 9, 2012 7 pages.
Oct. 6, 2011—(WO) International Search Report and Written Opinion—App PCT/US2011/035070.
Jurach, T. "Microsoft Outlook Quick Start Email Guide!" pp. 1-3 (2006).
Layar "What is Layar" <http://www.layar.com/features/> [retrieved Nov. 14, 2012] 7 pages.
Lorensen et al. "Marching Cubes: A high resolution 3D surface construction algorithm" In Computer Graphics, vol. 21, Nr. 4, Jul. 1987.
Lucero et al. "Pass-Them-Around: Collaborative User of Mobile Phones for Photo Sharing" CHI 2011—Session: Photo Sharing, May 7-11, 2011, Vancouver, BC, Canada, 10 pages.
Park et al. "Tunable Machine Vision-Based Strategy for Automated Annotation of Chemical Databases" Journal of Chemical Information and Modeling, vol. 49, No. 8, 2009, pp. 1993-2001.
Pering et al. "Enabling Pervasive Collaboration with Platform Composition" Intel Research Santa Clara, 2009, 18 pages.
Scheible et al., "MobiToss: A Novel gesture based interface for creating and sharing mobile multimedia art on large public displays" MM'08, Oct. 26-31, 2008 Vancouver British Columbia, Canada, pp. 957-960, 4 pages.
Tsotsis "Word Lens Translates Words Inside of Images. Yes Really. ," <http://techcrunch.com/2010/12/16/world-lens-translates-words-inside-of-images-yes-really/> [retrieved Nov. 14, 2012] Dec. 16, 2010, 3 pages.
Weinberg et al., "ZooZBeat: as Gesture-based Mobile Music Studio" NIME 2009, pp. 312-315, 4 pages.
Algorri et al., "Reconstruction of Chemical Molecules from Images" 2007 Annual International Conference of the IEEE Engineering in Medicine and Biology Society (EMBC 07) Lyon, France, Aug. 22-26, 2007, in Conjunction with the Biennial Conference of the Societe Francaise de Genie Biologique et Medical (SFGB) Aug. 22 2007, pp. 4609-4612.

Casey et al. "Optical Recognition of Chemical Graphics" Document Analysis and Recognition, 1993, Proceedings of the Second International Conference on, Tsukuba Science City, Japan, Oct. 20-22, 1993, Los Alamitos, CA, US IEEE Comput. Soc., Oct. 20, 1993, pp. 627-631.
Filippov et al. "Optical Structure Recognition Software to Recover Chemical Information: OSRA, An Open Source Solution" Journal of Chemical Information and Modeling, vol. 49, No. 3, Mar. 23, 2009, pp. 740-743.
Park et al., "Automated extraction of chemical structure information from digital raster images" Chemistry Central Journal, Biomed Central Ltd., vol. 3, No. 1, Feb. 5, 2009, pp. 1-16.
Valko et al., "CLiDE Pro: The Latest Generation of CLiDE, a Tool for Optical Chemical Structure Recognition" Journal of Chemical Information and Modeling, vol. 49, No. 4, Mar. 19, 2009, pp. 780-787.
Website: https://itunes.apple.com/nl/app/flick./id644265534?mt=8 (2013).
Website: http://getflick.io/ (2013).
Mar. 20, 2013—(WO) International Search Report and Written Opinion—App PCT/US2012/026574.
Kim, et al. "Development of a Gesture-Based Molecular Visualization Tool Based on Virtual Reality for Moleculara Docking" Bull. Korean Chem. Soc. 2004 vol. 25, No. 10, pp. 1571-1574.
Williams et al., "Mobile apps for chemistry in the wordl of drug discovery" Drug Discovery Today, vol. 16 Nos. 21/22, Nov. 2011, pp. 928-939.
Williams et al., "Smart Phones, a Powerful Tool in the Chemistry Classroom" Journal of Chemical Education, 2011, pp. 683-686.
Wobbrock, et al., "User-Defined Gestures for Surface Computing" CHI-Tabletop Gestures, Apr. 7, 2009, pp. 1083-1092.
"Chem & Bio Draw", Version 12.0, CambridgeSoft, Inc., 2009.
"ChemDraw User's Guide", Version 9.0.1, CambridgeSoft, Inc., Dec. 2004.
"IDBS Makes Chemical Structure Drawing Mobile", press release, ID Business Solutions, Ltd., Dec. 9, 2009.
Logtenberg, "Multi-user interaction with molecular visualizations on a multi-touch table" MSc thesis, Human Media Interaction Group, University of Twente, Aug. 11, 2009.
Mills, "ChemDraw Ultra 10.0" Journal of American Chemical Society, v. 128, n. 41, pp. 13649-13650, 2006.
"ChemJuice Grande—Basic Structure Drawing", printout page of YouTube video posting from IDBS at http://www.youtube.com/watch?v=mK0cC5bLzd0, uploaded Oct. 3, 2011, printed May 18, 2015.
"MolPrime+", http://molmatinf.com/molprimeplus.html, Molecular Materials Informatics, Inc., Jan. 23, 2011.
"Mobile Molecular DataSheet", http://molmatinf.com/mmdsios.html, Molecular Materials Informatics, Inc., Sep. 23, 2011, retrieved by Archive.org as https://web.archive.org/web/20120403140454/http://molmatinf.com/mmdsios.html on Apr. 3, 2012.
"Introduction to Drawing (iPhone)", http://molmatinf.com/introdrawios.html, Molecular Materials Informatics, Inc., Dec. 9, 2010, retrieved by Archive.org as https://web.archive.org/web/20120413131358/http://molmatinf.com/introdrawios.html on Apr. 13, 2012.
"Overview of Drawing Gestures (iPhone)", http://molmatinf.com/gesturesios.html, Molecular Materials Informatics, Inc., Nov. 3, 2010, retrieved by Archive.org as https://web.archive.org/web/20101118005114/http://molmatinf.com/gesturesios.html on Nov. 18, 2010.
"Van Der Waals Radius of the elements" retrieved from http://periodictable.com/Properties/A/VanDerWaalsRadius.v.html, May 22, 2008.
May 13, 2020—(EP) Notice of Allowance—App No. 12716771.6.
May 8, 2020—(CA) Notice of Allowance—App No. 2,865,004.
Jul. 2, 2020—(AU) Eamination Report—App No. 2019204427.

\* cited by examiner

SYSTEMS, METHODS, AND APPARATUS FOR DRAWING AND EDITING CHEMICAL STRUCTURES ON A USER INTERFACE VIA USER GESTURES

TECHNICAL FIELD

In various embodiments, the present invention relates to systems, methods, and apparatus for drawing chemical structures. More specifically, described herein are exemplary systems, methods, and apparatus for creating and editing representations of chemical structures using a touch and gesture based drawing tool.

BACKGROUND

Chemical structure rendering software is widely used by research and educational institutions to depict chemical structures and chemical reactions of interest. Unlike chemical formulas or chemical names, structural formulas provide a graphical representation of the molecular structure. A graphical chemical structure representation is capable of indicating the arrangements of atoms in a way that a chemical formula cannot.

Current methods for drawing and editing chemical structures on a computer utilize mouse-driven or touch pad commands that include pointing and clicking on displayed menu items in a graphical user interface. Existing chemical structure rendering 'apps' for tablet computers and other portable computing devices (e.g., portable phones) utilize the same menu-driven paradigm. In general, these approaches are manually intensive and non-intuitive.

There is a need for more efficient and intuitive user interfaces for drawing and editing chemical structures on a touch screen or touch pad of an electronic device. A particular need exists for electronic systems and devices that receive intuitive gesture input from a user's fingers on a touch screen or touch pad and utilize the input to create and edit chemical structure representations.

SUMMARY OF THE INVENTION

Described herein are various embodiments of systems, methods, and apparatus that allow a user to more intuitively draw and edit a chemical structure using one or more fingers on an input interface, such as a touch pad or touch screen. In various embodiments, the systems, methods, and apparatus utilize or include a tablet computer, a mobile phone device, or any other computer device or system capable of receiving input from a user's fingers. The systems, methods, and apparatus have applications in a wide variety of industries that create and edit structural formulas, such as the reagent industry, the publishing industry, and/or the web search industry. By incorporating intuitive, easy to perform gestures, the systems, methods, and apparatus described herein provide an efficient and accurate tool for drawing and editing chemical structures.

In general, in one aspect, embodiments of the invention feature an apparatus for creating a graphical representation of a chemical structure. A user may utilize the apparatus to assign an atom label to the chemical structure representation by performing a press and tap gesture. The apparatus includes: a touch pad or touch screen configured to receive input from a user; (b) a memory for storing a code defining a set of instructions; and (c) a processor for executing the set of instructions. The code includes a chemical structure drawing module configured to: (i) provide a representation of a chemical structure on a graphical display; (ii) receive a first signal corresponding to a user press gesture delivered upon the touch pad or touch screen at a location corresponding to a selected atom position in the chemical structure representation; (iii) receive a second signal corresponding to a user tap gesture delivered upon the touch pad or touch screen; (iv) upon receiving the second signal, provide a contextual menu that includes a plurality of atom labels on the graphical display; (v) receive a third signal corresponding to a user selection of one of the atom labels; and (vi) in the graphical display, update the chemical structure representation to include the selected atom label at the selected atom position in the chemical structure representation.

In certain embodiments, the apparatus includes a touch screen and the touch screen includes the graphical display. In preferred embodiments, the contextual menu actively excludes atom labels that would result in a chemically impossible structure if included at the selected atom position in the chemical structure representation. A location of the user tap gesture delivered upon the touch pad or touch screen is preferably near the location on the touch pad or touch screen corresponding to the selected atom position in the chemical structure representation.

In another aspect, embodiments of the invention feature an article of manufacture having computer-readable program portions embodied thereon for creating a graphical representation of a chemical structure. A user may use the article to assign an atom label to the chemical structure representation by performing a press and tap gesture. The article includes computer-readable instructions for: (i) providing a representation of a chemical structure on a graphical display; (ii) receiving a first signal corresponding to a user press gesture delivered upon a touch pad or touch screen at a location corresponding to a selected atom position in the chemical structure representation; (iii) receiving a second signal corresponding to a user tap gesture delivered upon the touch pad or touch screen; (iv) upon receiving the second signal, providing a contextual menu that includes a plurality of atom labels on the graphical display; (v) receiving a third signal corresponding to a user selection of one of the atom labels; and (vi) in the graphical display, updating the chemical structure representation to include the selected atom label at the selected atom position in the chemical structure representation. The description of elements of the embodiments above can be applied to this aspect of the invention as well.

In another aspect, embodiments of the invention feature a computer-implemented method of creating a graphical representation of a chemical structure. A user may use the method to assign an atom label to the chemical structure representation by performing a press and tap gesture. The computer-implemented method includes the steps of: (i) providing a representation of a chemical structure on a graphical display; (ii) receiving a first signal corresponding to a user press gesture delivered upon a touch pad or touch screen at a location corresponding to a selected atom position in the chemical structure representation; (iii) receiving a second signal corresponding to a user tap gesture delivered upon the touch pad or touch screen; (iv) upon receiving the second signal, providing a contextual menu that includes a plurality of atom labels on the graphical display; (v) receiving a third signal corresponding to a user selection of one of the atom labels; and (vi) in the graphical display, updating the chemical structure representation to include the selected atom label at the selected atom position in the chemical structure representation. The description of elements of the embodiments above can be applied to this aspect of the invention as well.

In another aspect, the invention relates to an apparatus for creating a graphical representation of a chemical structure. A user may utilize the apparatus to change a chemical bond characteristic within the chemical structure representation by performing a tap gesture. The apparatus includes: (a) a touch pad or touch screen configured to receive input from a user; (b) a memory for storing a code defining a set of instructions; and (c) a processor for executing the set of instructions. The code includes a chemical structure drawing module configured to: (i) provide a representation of a chemical structure on a graphical display; (ii) receive a first signal corresponding to a first user tap gesture delivered upon the touch pad or touch screen at a location corresponding to a selected chemical bond position in the chemical structure representation; and (iii) upon receiving the first signal, updating a representation of a chemical bond at the selected chemical bond position of the chemical structure representation. The description of elements of the embodiments above can be applied to this aspect of the invention as well.

In certain embodiments, the chemical structure drawing module is configured to toggle through a contextual selection of bond order representations at the selected chemical bond position upon receiving signals corresponding to repeated user tap gestures. In one embodiment, the contextual selection of bond order representations actively excludes bond orders that would result in a chemically impossible structure if included at the selected chemical bond position in the chemical structure representation. The chemical structure drawing module is preferably further configured to, upon receiving a second signal corresponding to a second user tap gesture delivered upon the touch pad or touch screen at a location corresponding to a selected chemical bond position in the chemical structure representation, update a representation of stereochemistry at the selected chemical bond position. In some embodiments, the chemical structure drawing module is configured to toggle through a contextual selection of stereochemistry representations at the selected chemical bond position upon receiving signals corresponding to repeated user tap gestures. The chemical structure drawing module is preferably configured to distinguish between the first user tap gesture and the second user tap gesture, wherein one gesture is provided by one finger, and the other is provided by two or more fingers.

In another aspect, embodiments of the invention feature an article of manufacture having computer-readable program portions embodied thereon for creating a graphical representation of a chemical structure. A user may utilize the article to change a chemical bond characteristic within the chemical structure representation by performing a tap gesture. The article includes computer-readable instructions for: (i) providing a representation of a chemical structure on a graphical display; (ii) receiving a first signal corresponding to a first user tap gesture delivered upon a touch pad or touch screen at a location corresponding to a selected chemical bond position in the chemical structure representation; and (iii) upon receiving the first signal, updating a representation of a chemical bond at the selected chemical bond position of the chemical structure representation. The description of elements of the embodiments above can be applied to this aspect of the invention as well.

In another aspect, the invention relates to a computer-implemented method of creating a graphical representation of a chemical structure. A user may utilize the method to change a chemical bond characteristic within the chemical structure representation by performing a tap gesture. The computer-implemented method includes the steps of: (i) providing a representation of a chemical structure on a graphical display; (ii) receiving a first signal corresponding to a first user tap gesture delivered upon a touch pad or touch screen at a location corresponding to a selected chemical bond position in the chemical structure representation; and (iii) upon receiving the first signal, updating a representation of a chemical bond at the selected chemical bond position of the chemical structure representation. The description of elements of the embodiments above can be applied to this aspect of the invention as well.

In another aspect, embodiments of the invention feature an apparatus for creating a graphical representation of a chemical structure. A user may utilize the apparatus to lengthen a molecular chain of the chemical structure representation by performing a drag gesture. The apparatus includes (a) a touch pad or touch screen configured to receive input from a user; (b) a memory for storing a code defining a set of instructions; and (c) a processor for executing the set of instructions. The code includes a chemical structure drawing module configured to: (i) provide a representation of a chemical structure on a graphical display; (ii) receive a signal corresponding to a user drag gesture delivered upon the touch pad or touch screen at a location corresponding to a selected atom position in the chemical structure representation, wherein the user drag gesture includes a drag length; and (iii) upon receiving the signal, update the chemical structure representation by extending a molecular chain from the selected atom position, wherein length of the extended molecular chain corresponds to the drag length. The description of elements of the embodiments above can be applied to this aspect of the invention as well.

In another aspect, embodiments of the invention feature an article of manufacture having computer-readable program portions embodied thereon for creating a graphical representation of a chemical structure. A user may utilize the article to lengthen a molecular chain of the chemical structure representation by performing a drag gesture. The article includes computer-readable instructions for: (i) providing a representation of a chemical structure on a graphical display; (ii) receiving a signal corresponding to a user drag gesture delivered upon a touch pad or touch screen at a location corresponding to a selected atom position in the chemical structure representation, wherein the user drag gesture includes a drag length; and (iii) upon receiving the signal, updating the chemical structure representation by extending a molecular chain from the selected atom position, wherein length of the extended molecular chain corresponds to the drag length. The description of elements of the embodiments above can be applied to this aspect of the invention as well.

In another aspect, the invention relates to a computer-implemented method of creating a graphical representation of a chemical structure. A user may utilize the method to lengthen a molecular chain of the chemical structure representation by performing a drag gesture. The computer-implemented method includes the steps of: (i) providing a representation of a chemical structure on a graphical display; (ii) receiving a signal corresponding to a user drag gesture delivered upon a touch pad or touch screen at a location corresponding to a selected atom position in the chemical structure representation, wherein the user drag gesture includes a drag length; and (iii) upon receiving the signal, updating the chemical structure representation by extending a molecular chain from the selected atom position, wherein length of the extended molecular chain corresponds to the drag length. The description of elements of the embodiments above can be applied to this aspect of the invention as well.

In another aspect, embodiments of the invention feature an apparatus for creating a graphical representation of a chemical structure. A user may utilize the apparatus to rotate the chemical structure representation by performing a rotation gesture. The apparatus includes: (a) a touch pad or touch screen configured to receive input from a user; (b) a memory for storing a code defining a set of instructions; and (c) a processor for executing the set of instructions. The code includes a chemical structure drawing module configured to (i) provide a representation of a chemical structure on a graphical display, and (ii) receive a signal corresponding to at least one of a first, second, and third user rotation gesture delivered upon the touch pad or touch screen at or near a location corresponding to the chemical structure representation. The first user rotation gesture includes a two-handed spin when the user contacts the touch pad or touch screen with a first finger of a first hand and a second finger of a second hand and translates the first finger and the second finger in a common rotational direction around a point between the first and second fingers on the touch pad or touch screen. The second user rotation gesture includes an anchored spin when the user contacts the touch pad or touch screen with a first finger at a location corresponding to an atom position in the chemical structure representation, contacts the touch pad or touch screen with a second finger, and translates the second finger on the touch pad or touch screen in an arc around the location corresponding to a selected atom position in the chemical structure representation. The third user rotation gesture includes a two-fingered rotation when the user contacts the touch pad or touch screen with two figures at a location corresponding to the chemical structure and drags the two fingers along the touch pad or touch screen in an arc. The chemical structure drawing module is also configured to, (iii) upon receiving the signal, update a rotational position of the chemical structure representation. The description of elements of the embodiments above can be applied to this aspect of the invention as well.

In certain embodiments, the chemical structure drawing module is configured to update the rotational position of the chemical structure representation in response to the first user rotation gesture by rotating the chemical structure about a point corresponding to the point between the first and second fingers on the touch pad or touch screen. In one embodiment, the chemical structure drawing module is configured to update the rotational position of the chemical structure representation in response to the second user rotation gesture by rotating the chemical structure about the selected atom position. In some embodiments, the chemical structure drawing module is configured to update the rotational position of the chemical structure representation in response to the third user rotation gesture by rotating the chemical structure about a substantially central point of the chemical structure.

In another aspect, embodiments of the invention relate to an article of manufacture having computer-readable program portions embodied thereon for creating a graphical representation of a chemical structure. A user may utilize the article to rotate the chemical structure representation by performing a rotation gesture. The article includes computer-readable instructions for (i) providing a representation of a chemical structure on a graphical display, and (ii) receiving a signal corresponding to at least one of a first, second, and third user rotation gesture delivered upon a touch pad or touch screen at or near a location corresponding to the chemical structure representation. The first user rotation gesture includes a two-handed spin when the user contacts the touch pad or touch screen with a first finger of a first hand and a second finger of a second hand and translates the first finger and the second finger in a common rotational direction around a point between the first and second fingers on the touch pad or touch screen. The second user rotation gesture includes an anchored spin when the user contacts the touch pad or touch screen with a first finger at a location corresponding to an atom position in the chemical structure representation, contacts the touch pad or touch screen with a second finger, and translates the second finger on the touch pad or touch screen in an arc around the location corresponding to a selected atom position in the chemical structure representation. The third user rotation gesture includes a two-fingered rotation when the user contacts the touch pad or touch screen with two figures at a location corresponding to the chemical structure and drags the two fingers along the touch pad or touch screen in an arc. The article also includes computer-readable instructions for, (iii) upon receiving the signal, updating a rotational position of the chemical structure representation. The description of elements of the embodiments above can be applied to this aspect of the invention as well.

In another aspect, the invention relates to a computer-implemented method of creating a graphical representation of a chemical structure. A user may utilize the method to rotate the chemical structure representation by performing a rotation gesture. The computer-implemented method includes the steps of (i) providing a representation of a chemical structure on a graphical display, and (ii) receiving a signal corresponding to at least one of a first, second, and third user rotation gesture delivered upon a touch pad or touch screen at or near a location corresponding to the chemical structure representation. The first user rotation gesture includes a two-handed spin when the user contacts the touch pad or touch screen with a first finger of a first hand and a second finger of a second hand and translates the first finger and the second finger in a common rotational direction around a point between the first and second fingers on the touch pad or touch screen. The second user rotation gesture includes an anchored spin when the user contacts the touch pad or touch screen with a first finger at a location corresponding to an atom position in the chemical structure representation, contacts the touch pad or touch screen with a second finger, and translates the second finger on the touch pad or touch screen in an arc around the location corresponding to a selected atom position in the chemical structure representation. The third user rotation gesture includes a two-fingered rotation when the user contacts the touch pad or touch screen with two figures at a location corresponding to the chemical structure and drags the two fingers along the touch pad or touch screen in an arc. The method also includes the step of, (iii) upon receiving the signal, updating a rotational position of the chemical structure representation. The description of elements of the embodiments above can be applied to this aspect of the invention as well.

In another aspect, embodiments of the invention relate to a computer-implemented method of creating a graphical representation of a chemical structure. A user may utilize the method to edit a chemical structure representation by performing a pinch-zoom gesture. The computer-implemented method includes the steps of: (i) providing a representation of a chemical structure on a graphical display; (ii) receiving a first signal corresponding to a user multi-finger gesture delivered upon a touch pad or touch screen at a location corresponding to the chemical structure representation; and, (iii) upon receiving the first signal, (A) providing a working view of the chemical structure representation on the graphical display, wherein the working view is scaled such that individual atoms and/or bonds within the chemical structure representation are independently accessible to fingertips of the user, and (B) providing a full view of the chemical structure representation in a corner of the graphical display. The description of elements of the embodiments above can be applied to this aspect of the invention as well.

In certain embodiments, the method includes the steps of: (iv) receiving a second signal corresponding to a user tap gesture delivered upon the touch pad or touch screen at a location in the working view corresponding to an atom or bond in the chemical structure representation; and (v) after receiving the second signal, updating the chemical structure representation at the location according to a selection from a menu on the graphical display, wherein the menu includes representations of chemical structure elements. In some embodiments, the chemical structure representation in the working view is at least partially transparent. The multi-finger gesture may include a pinch-to-zoom gesture. In one embodiment, the working view is active and the full view is inactive. A map may be superimposed on the full view indicating boundaries of the chemical structure representation currently viewable in the working view.

In another aspect, embodiments of the invention feature a computer-implemented method of creating a graphical representation of a chemical structure. A user may utilize the method to join two chemical structure representations together by performing a pinch gesture. The computer-implemented method includes the steps of: (i) providing a representation of a first chemical structure and a representation of a second chemical structure on a graphical display; (ii) receiving a signal corresponding to a user pinch gesture delivered upon a touch pad or touch screen; and (iii) upon receiving the signal, joining the representation of the first chemical structure and the representation of the second chemical structure at or in the vicinity of the first and second structure elements to produce a representation of a third chemical structure. The pinch gesture originates at a first location and a second location. The first location corresponds to a first structure element on the representation of the first chemical structure, and the second location corresponds to a second structure element on the representation of the second chemical structure. The description of elements of the embodiments above can be applied to this aspect of the invention as well.

In certain embodiments, the first and second structure elements include an atom and/or a bond. In one embodiment, the method includes joining the representation of the first chemical structure and the representation of the second chemical structure according to a set of chemical structure rules.

In another aspect, embodiments of the invention feature a computer-implemented method of creating a graphical representation of a chemical structure. A user may utilize the method to join two chemical structure representations together by performing a fling gesture. The computer-implemented method includes the steps of: (i) providing a representation of a chemical structure on a graphical display; (ii) providing a menu on the graphical display, wherein the menu includes representations of chemical structure elements; (iii) receiving a first signal corresponding to a user tap gesture delivered upon a touch pad or touch screen at a first location corresponding to a target on the chemical structure representation; (iv) receiving a second signal corresponding to a user fling gesture delivered upon the touch pad or touch screen, wherein the fling gesture originates at a second location corresponding to a representation of a chemical structure element in the menu and proceeds in a direction towards the first location; and (v) upon receiving the first and second signals, joining the representation of the chemical structure element with the chemical structure representation at the target to create a representation of a new chemical structure. The description of elements of the embodiments above can be applied to this aspect of the invention as well.

In certain embodiments, the method includes joining the representation of the chemical structure element with the chemical structure representation according to a set of chemical structure rules. In various embodiments, the joining step includes animating the representation of the chemical structure element from the second location to the first location on the graphical display, in response to the fling gesture. The tap gesture may include a tap and hold gesture.

In another aspect, the invention relates to a computer-implemented method of creating a graphical representation of a chemical structure. A user may utilize the method to rotate the chemical structure representation by performing a flick gesture. The computer-implemented method includes the steps of: (i) providing a representation of a chemical structure on a graphical display; (ii) receiving a first signal corresponding to a user tap gesture delivered upon a touch pad or touch screen at a first location corresponding to the chemical structure representation; (iii) receiving a second signal corresponding to a user flick gesture delivered upon the touch pad or touch screen, wherein the flick gesture originates at a second location and proceeds in a flick direction, wherein the flick direction is substantially orthogonal to a line between the first location and the second location; and (iv) upon receiving the first and second signals, rotating the chemical structure representation in the flick direction about an axis of rotation, wherein the axis rotation is perpendicular to the graphical display and passes through the first location. The description of elements of the embodiments above can be applied to this aspect of the invention as well.

In certain embodiments, a velocity of rotation of the chemical structure representation corresponds to a velocity of the flick gesture. In one embodiment, the rotating step includes reducing a velocity of rotation of the chemical structure representation following the flick gesture.

In another aspect, embodiments of the invention feature a computer-implemented method of creating a graphical representation of a chemical structure. A user may utilize the method to create an electronic document for a chemical structure representation by performing a drag gesture. The computer-implemented method includes the steps of: (i) providing a representation of a chemical structure on a graphical display; (ii) receiving a first signal corresponding to a user drag gesture delivered upon a touch pad or touch screen at a location corresponding to empty space around the chemical structure representation; (iii) upon receiving the first signal, (A) translating the representation of the chemical structure in a direction corresponding to the drag gesture, and (B) providing an indication on the graphical display that release of the drag gesture will create a new electronic document for a chemical structure representation; (iv) receiving a second signal corresponding to release of the drag gesture delivered upon the touch pad or the touch screen; and (v) upon receiving the second signal, creating the new electronic document. In certain embodiments, the new electronic document includes the representation of the chemical structure. The description of elements of the embodiments above can be applied to this aspect of the invention as well.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

DESCRIPTION

Figure 1:
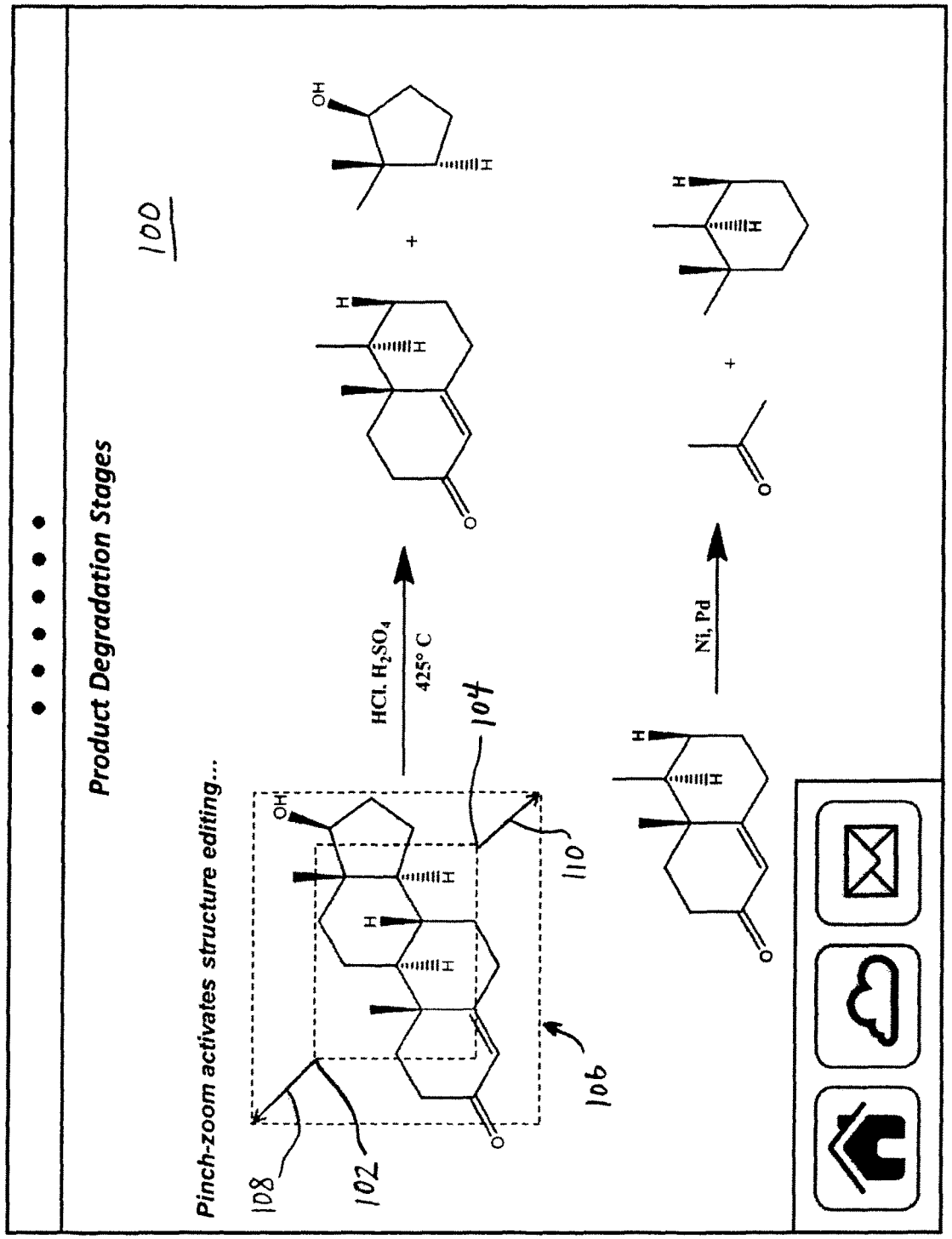
FIG. 1 is a schematic screenshot depicting a chemical structure representation and a pinch-zoom gesture for activating chemical structure editing, in accordance with an illustrative embodiment of the invention.

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

In general, in various embodiments, the present invention pertains to apparatus, systems, and methods for drawing chemical structures (e.g., a skeletal formula) on a computer having an input interface that interacts with the human hand. The computer may be, for example, a personal computer, a workstation, a tablet computer (e.g., an IPAD®), or a mobile phone device. In certain embodiments, the input interface is a touch screen or a touch pad (e.g., a mouse pad). For example, the user may interact directly with a touch screen to edit or create chemical structure representations that are displayed on the touch screen. Alternatively, the user may interact with a touch pad to edit or create chemical structure representations that are displayed on a separate graphical display (e.g., a computer monitor).

In certain embodiments, the user edits or creates chemical structure representations by performing a multi-touch gesture on the input interface. The multi-touch gesture may be as simple as contacting the input interface with one or two fingers to trace out a particular molecular structure or bond pattern, or as intricate as contacting the input interface with all the fingers of both hands in a complex sequence of movements, reminiscent of American Sign Language. In one embodiment, each motion of hands and fingers, whether complex or not, conveys a specific molecular editing sequence or action that is acted upon by the computer apparatus or system at the behest of the scientist.

In various embodiments, a user of the apparatus or system performs a gesture (e.g., a multi-touch gesture) by contacting the input interface with one or more fingertips. Alternatively, the user may perform the gesture by contacting the input interface with one or more other body parts (e.g., a knuckle or a hand), or with a device or object that is grasped or otherwise held by the user. For example, the user may perform the gesture using a hand-held stylus. Throughout this description, where a gesture is described as being performed with a user's fingers, it is contemplated that the gesture may be performed with the user's fingertips, knuckles, or other body part(s), and/or with a separate device or object manipulated by the user.

In certain embodiments, a user performs a tap gesture by contacting the input interface with a fingertip and bouncing or quickly removing the fingertip from the input interface. By contrast, in certain embodiments, a user performs a tap and hold gesture by contacting the input interface at a location with a fingertip and maintaining contact between the fingertip and the location for a desired period of time.

In various embodiments, the apparatus, systems, and methods utilize a set of rules for determining whether structural formulas requested by the user are chemically valid. In one embodiment, the rules are used to prevent the user from creating invalid structural formulas. For example, if the user attempts to add a triple bond to a chemical structure representation and the triple bond is not feasible, the user may be prevented from adding the triple bond. Likewise, if the user attempts to introduce a stereo chemical bond assignment that is not chemically valid, the user may be prevented from introducing the stereo chemical bond assignment. Similar rules may be used to prevent the user from adding structural elements, such as bonds or atoms, to a chemical structure representation that would result in a chemically invalid structure. In one embodiment, the rules are used to determine one or more "snap-to" positions at locations of feasible attachment of a group or structural element the user is attempting to add to the chemical structure representation.

Referring to FIG. 1, in certain embodiments, a user activates chemical structure editing by performing a pinch-zoom gesture on an input interface 100 (e.g., a touch screen). The user performs the pinch-zoom gesture by contacting the input interface 100 with a first finger at a first location 102 and a second finger at a second location 104. The first location 102 and the second location 104 correspond generally to a position of a chemical structure representation 106 in a graphical display or touch screen. While maintaining contact with the input interface 100, the user then drags the first finger in a first direction 108 and the second finger in a second, substantially opposite direction 110, along the input interface 100. In one embodiment, the fingers are dragged along the input interface 100 as though the user were trying to pull apart or stretch the chemical structure representation 106 within the graphical display.

Figure 2:
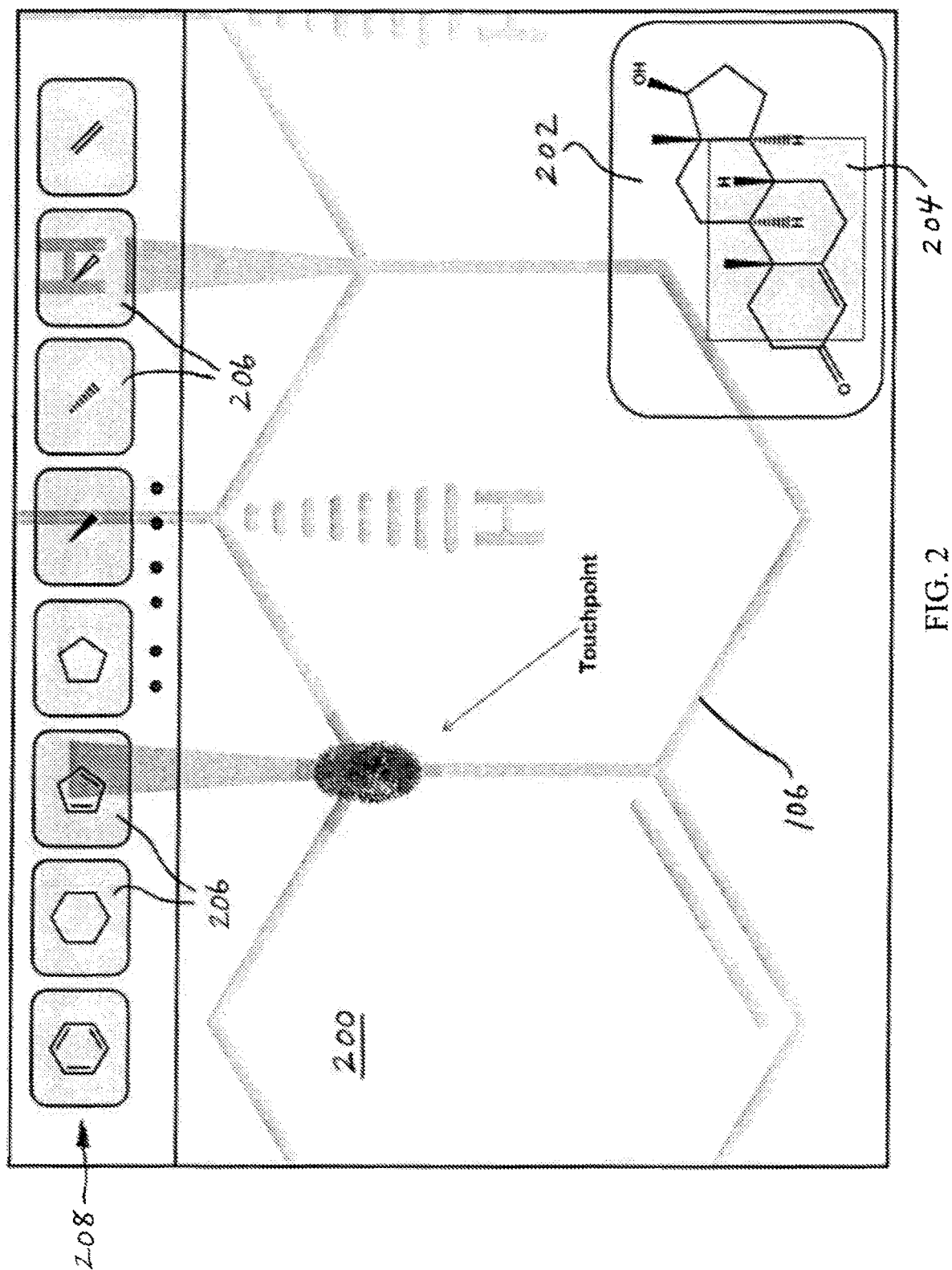
FIG. 2 is a schematic screenshot depicting a working view and a full view of a chemical structure representation, in accordance with an illustrative embodiment of the invention.

Referring to FIG. 2, upon receiving the pinch-zoom gesture, the computer or electronic device enters a chemical structure editing mode in which a working view 200 of the chemical structure representation 106 is provided on the graphical display. The working view 200 is scaled such that individual atoms and/or bonds within the chemical structure representation 106 may be independently accessed or selected by the user's fingers. A full view 202 of the chemical structure representation 106 is provided in a corner of the graphical display. The working view 200 is active (i.e., may be selected, manipulated, and/or edited by the user) and the full view 202 is inactive. A map or context box 204 is superimposed on the full view 202 to indicate boundaries of the chemical structure representation 106 currently viewable in the working view 200. In certain embodiments, the chemical structure representation 106 in the working view 200 is at least partially transparent.

In the working view 200, the user may edit the chemical structure representation 106 by selecting an atom or bond location in the chemical structure representation. The atom or bond location may be selected by, for example, delivering a tap gesture upon the input interface at a location corresponding to the atom or bond in the working view. The user may then modify the chemical structure representation 106 at the atom or bond location by selecting a representation of a chemical structure element 206 from a menu 208 on the graphical display. For example, the user may select the chemical structure element 206 by tapping the input interface 100 at a location corresponding to the chemical structure element 206. In one embodiment, selecting the chemical structure element 206 adds the chemical structure element 206 to the chemical structure representation 106 at the atom or bond location.

Figure 3:
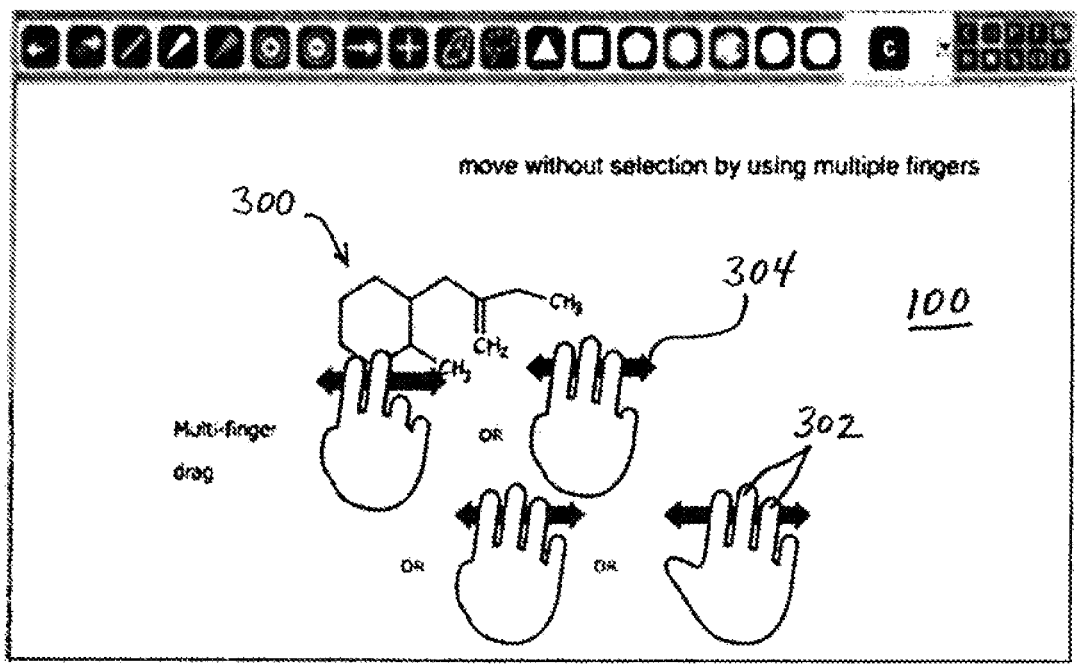
FIG. 3 is a schematic screenshot depicting a multi-touch drag gesture for translating a chemical structure representation in a graphical display, in accordance with an illustrative embodiment of the invention.

Referring to FIG. 3, in certain embodiments, the user translates a chemical structure representation 300 within the graphical display (e.g., in the working view) using a multi-touch drag gesture. The user performs the multi-touch drag gesture by contacting the input interface 100 with two or more fingers 302 in a location corresponding to the chemical structure representation 300. The two or more fingers 302 are then dragged along the input interface 100 in a direction 304 corresponding to the desired translation of the chemical structure representation 300. For example, if the user wishes to translate the chemical structure representation 300 to the right in the graphical display, the fingers 302 are dragged along the input interface 100 to the right. When the chemical structure representation 300 has been translated to the desired position, the fingers 302 are removed from the input interface 100.

Figure 4:
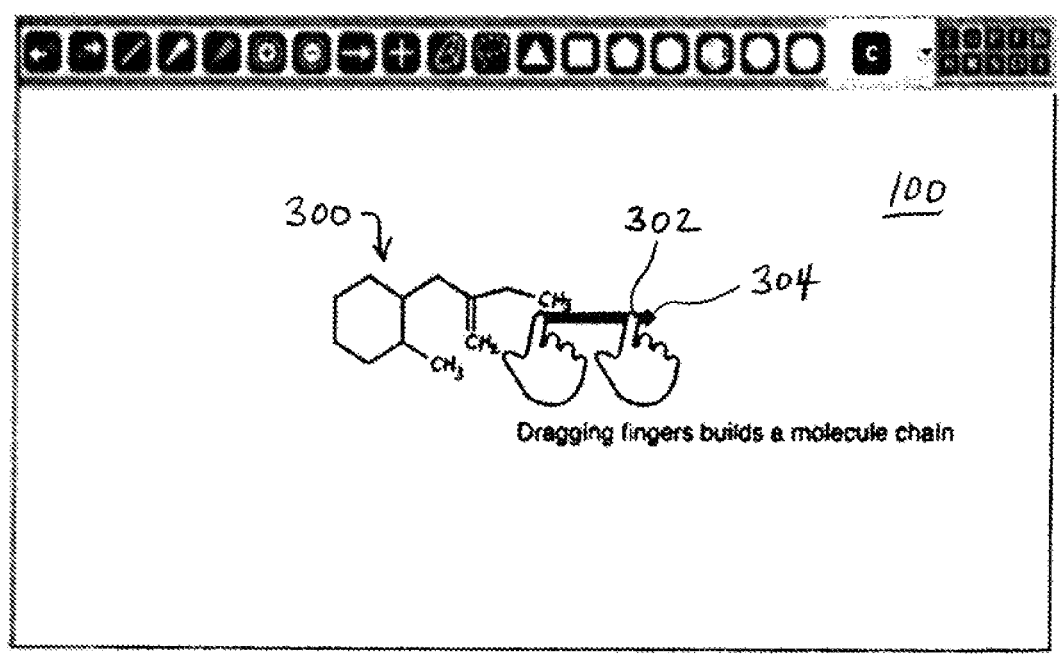
FIG. 4 is a schematic screenshot depicting a drag gesture for lengthening a molecular chain in a chemical structure representation, in accordance with an illustrative embodiment of the invention.

Referring to FIG. 4, in certain embodiments, the user builds or lengthens a molecular chain in the chemical structure representation 300 by performing a drag gesture. To perform the drag gesture, the user contacts the input interface 100 with a finger 302 at a location corresponding to an atom (e.g., an atom in an alkyl group) in the chemical structure representation 300. The finger 302 is then dragged along the input interface 100 by a length and direction 304 corresponding to the desired molecular chain length and direction. When the desired drag has been achieved, the finger 302 is removed from the input interface 100. During or after performance of the drag gesture, a representation of the new or lengthened molecular chain is added to the chemical structure representation 300 at the selected atom location.

Figure 5:
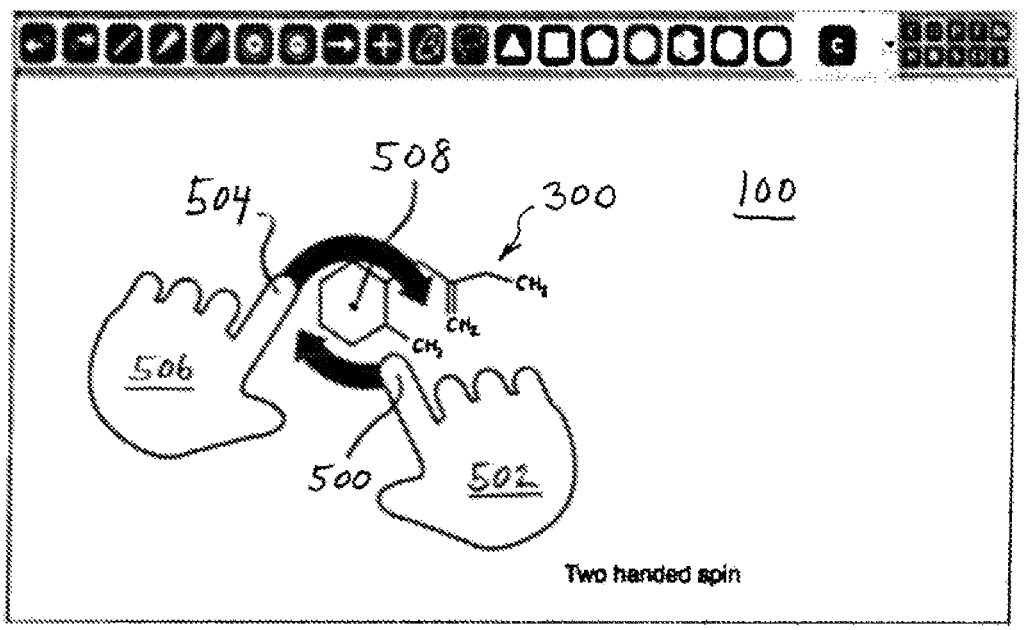
FIG. 5 is a schematic screenshot depicting a two-handed spin gesture for rotating a chemical structure representation in a graphical display, in accordance with an illustrative embodiment of the invention.

In certain embodiments, the user rotates the chemical structure representation within the graphical display (e.g., the working view) by performing one or more rotation gestures on the input interface 100. For example, in the embodiment depicted in FIG. 5, the user rotates the chemical structure representation 300 by performing a two-handed spin gesture. To perform the two-handed spin gesture, the user contacts the input interface 100 with a first finger 500 of a first hand 502 and a second finger 504 of a second hand 506. The first finger 500 and the second finger 504 are then dragged in a common rotational direction around a pivot point 508 between the first and second fingers 500, 504 on the input interface 100. Alternatively, the two-handed spin gesture may be performed using two fingers from the same hand. Upon receiving the two-handed spin gesture, the chemical structure representation 300 is rotated in the graphical display about an axis of rotation that passes through the pivot point 508 in a direction perpendicular to the graphical display. In general, an extent of the rotation of the chemical structure representation 300 corresponds to a distance the first and second fingers 500, 504 are translated around the pivot point 508.

Figure 6:
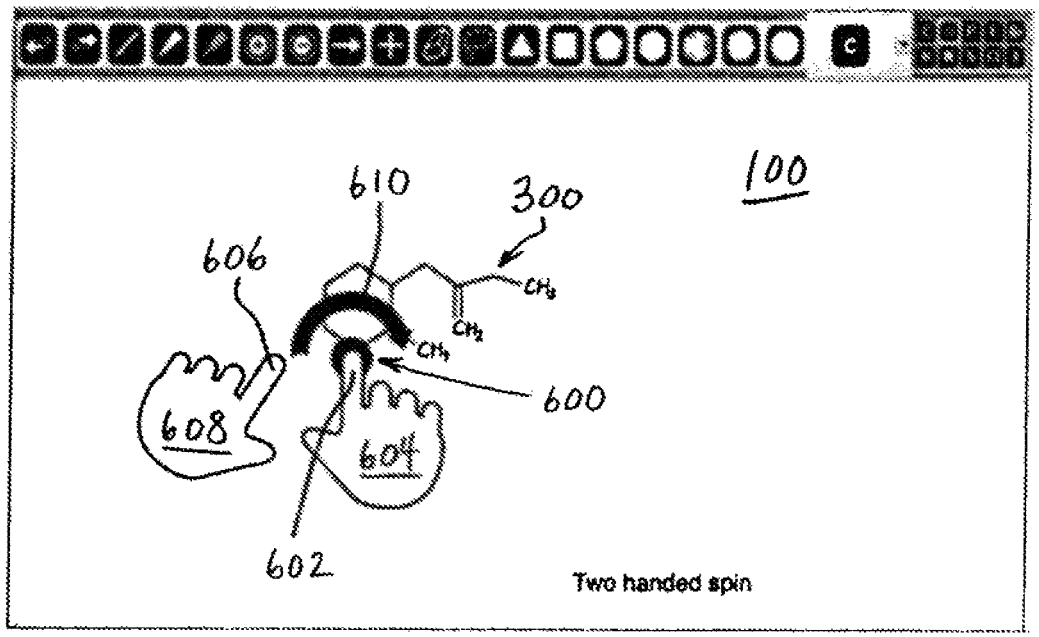
FIG. 6 is a schematic screenshot depicting an anchored spin gesture for rotating a chemical structure representation in a graphical display, in accordance with an illustrative embodiment of the invention.

Referring to FIG. 6, in certain embodiments, the user rotates the chemical structure representation 300 by performing an anchored spin gesture. To perform the anchored spin gesture, the user selects an atom position 600 by contacting the input interface 100 with a first finger 602 of a first hand 604 at a location corresponding to the atom position 600 in the chemical structure representation 300. The user then contacts the input interface 100 with a second finger 606 of a second hand 608 and drags or translates the second finger 606 along the input interface 100 in an arc 610 around the first finger 602. Upon receiving the anchored spin gesture, the chemical structure representation 300 is rotated about an axis of rotation that passes through the selected atom position 600 (i.e., the anchor position) in a direction perpendicular to the graphical display. In general, the extent of the rotation of the chemical structure representation 300 corresponds to a distance the second finger 606 is translated around the first finger 602.

Figure 7:
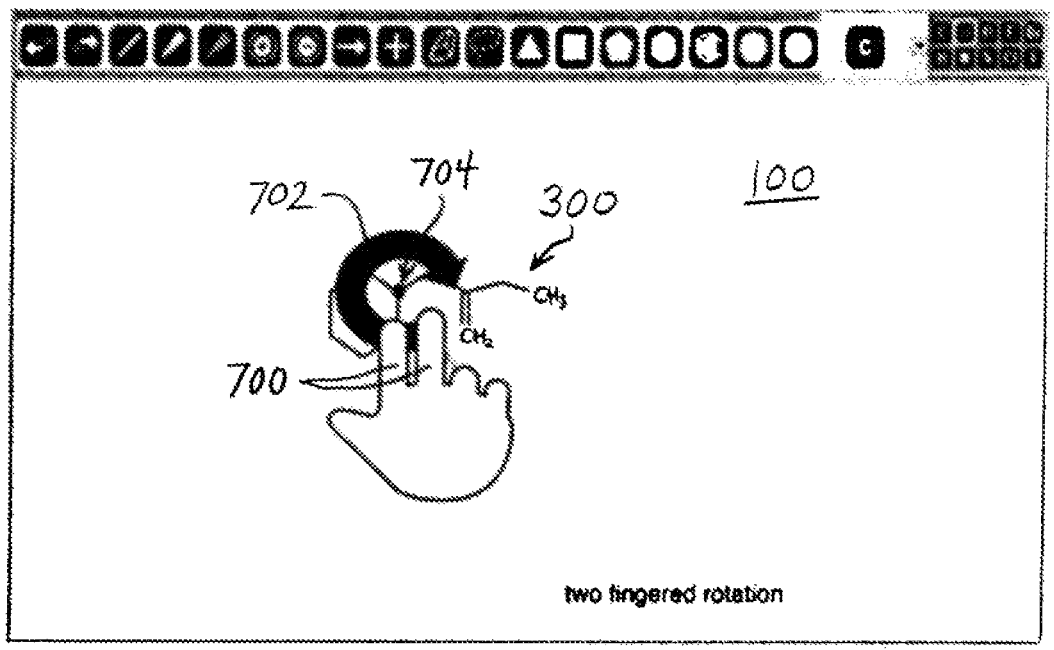
FIG. 7 is a schematic screenshot depicting a two-fingered rotation gesture for rotating a chemical structure representation in a graphical display, in accordance with an illustrative embodiment of the invention.

Referring to FIG. 7, in various embodiments, the user rotates the chemical structure representation 300 by performing a two-fingered rotation gesture. To perform the two-fingered rotation gesture, the user contacts the input interface 100 with two (or more) fingers 700 at a location corresponding to the chemical structure representation 300 and drags the two fingers 700 along the input interface 100 in an arc 702 around a pivot point 704. In a typical embodiment, the user contacts the input interface 100 with an index finger and a middle finger of the same hand and moves the fingers and the hand as a rigid body along the input interface 100 to form the arc 702. In this way, a distance and/or orientation between the two fingers 700 may remain substantially constant during the performance of the two-fingered rotation gesture. Upon receiving the two-fingered rotation gesture, the chemical structure representation 300 is rotated about an axis of rotation that passes through the pivot point 704 in a direction perpendicular to the graphical display. In general, the extent of the rotation of the chemical structure representation 300 corresponds to a distance the two fingers 700 travel along the arc. In certain embodiments, the systems, apparatus, and methods recognize that the user is requesting a rotation of the chemical structure representation 300 when one of the user's fingers moves in an arc along the input interface 100. By contrast, referring again to FIG. 3, the systems, apparatus, and methods may recognize that the user is requesting a translation of the chemical structure representation 300 when one of the user's fingers moves in a straight line (e.g., right, left, up, or down) along the input interface 100.

Figure 8:
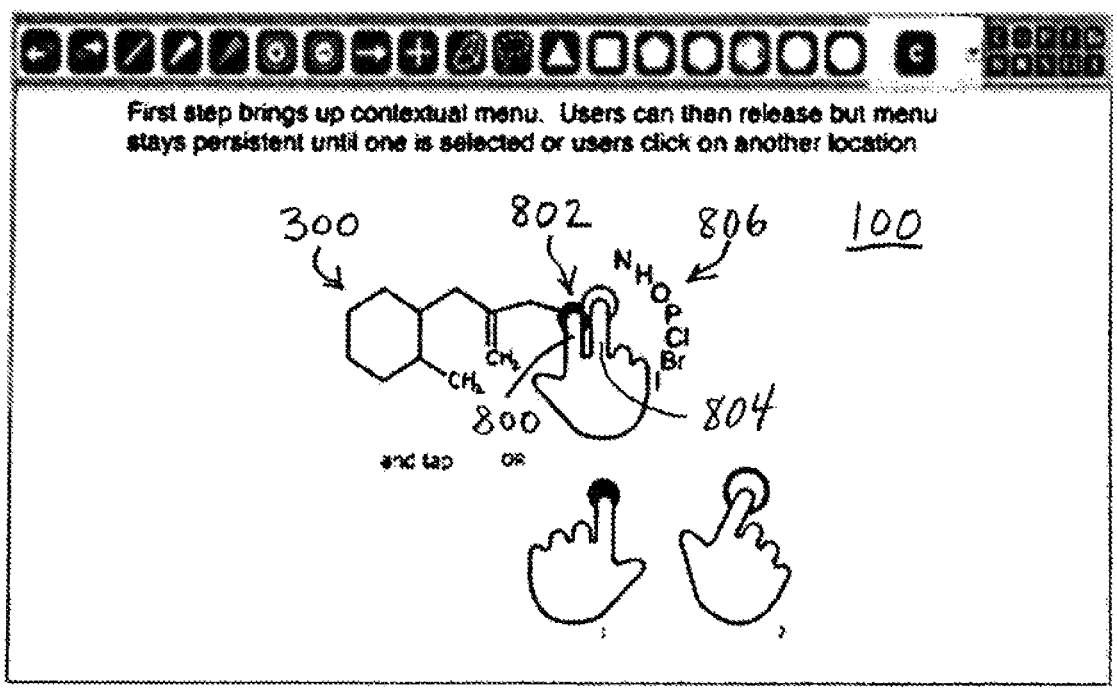
FIGS. 8 and 9 are schematic screenshots depicting a press and tap gesture for changing an atom label in a chemical structure representation, in accordance with an illustrative embodiment of the invention.
Figure 9:
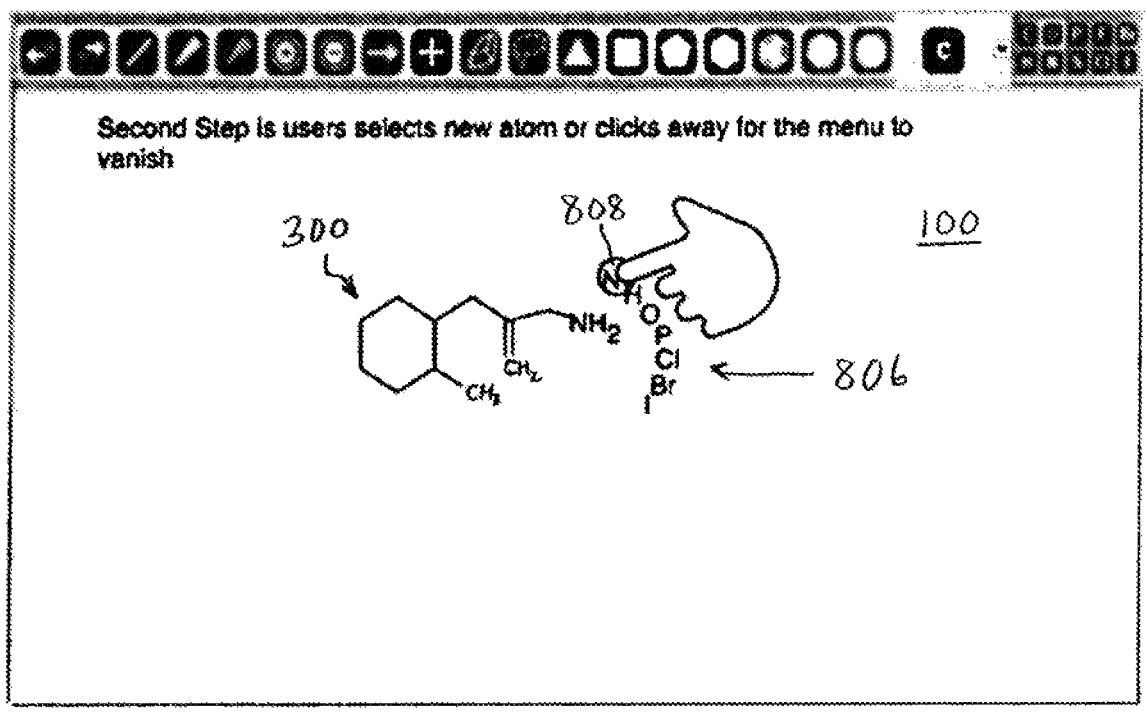

In the embodiment depicted in FIGS. 8 and 9, the user changes an atom label in the chemical structure representation 300 by performing a press and tap gesture. To perform the press and tap gesture, the user presses the input interface 100 with a first finger 800 at a location corresponding to an atom location 802 in the chemical structure representation 300. While pressing the input interface 100 with the first finger 800, the user taps the input interface 100 with a second finger 804. The first finger 800 and the second finger 804 may be from the same hand or from different hands. Upon delivering the tap from the second finger 804, a contextual menu 806 having a selection of atom labels 808 is provided on the graphical display. Referring to FIG. 9, the user may now select one of the atom labels 808 by tapping or contacting the input interface 100 at a location corresponding to a desired atom label 808. After selecting the atom label 808, the atom label 808 is added to the chemical structure representation 300 at the atom location 802. In one embodiment, to remove the contextual menu 806 from the graphical display, the user taps or contacts the input interface 100 at a location corresponding to a position outside of the contextual menu 806.

Figure 10:
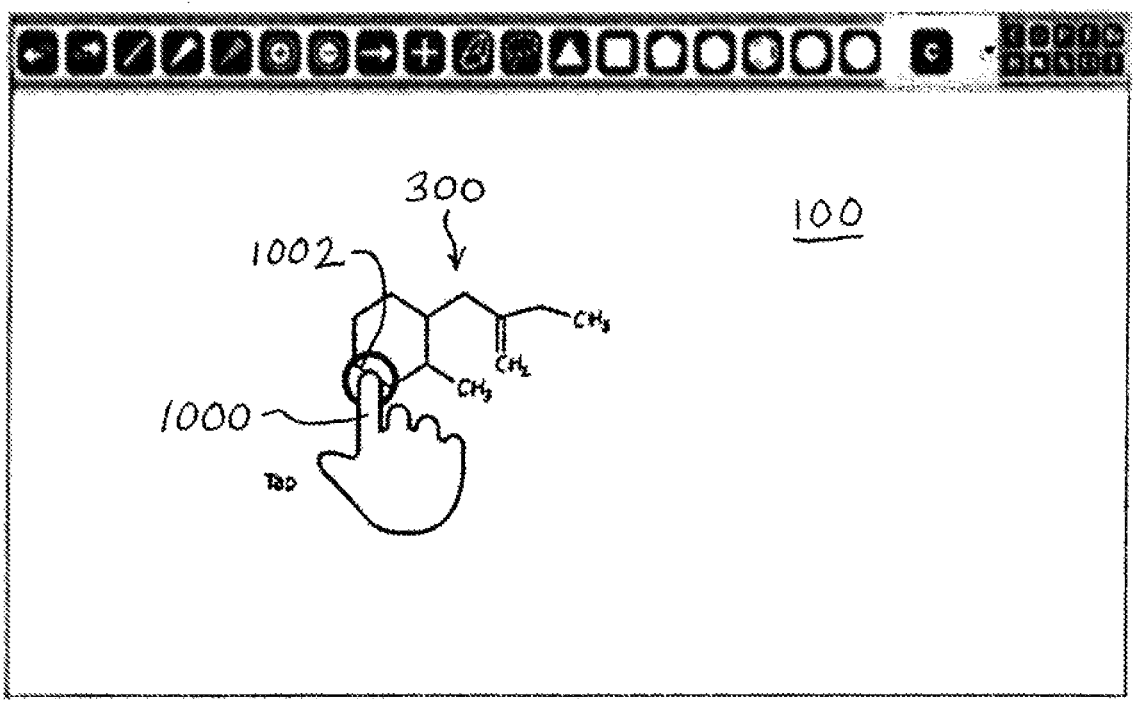
FIGS. 10 and 11 are schematic screenshots depicting a bond tap gesture for changing a bond order in a chemical structure representation, in accordance with an illustrative embodiment of the invention.
Figure 11:
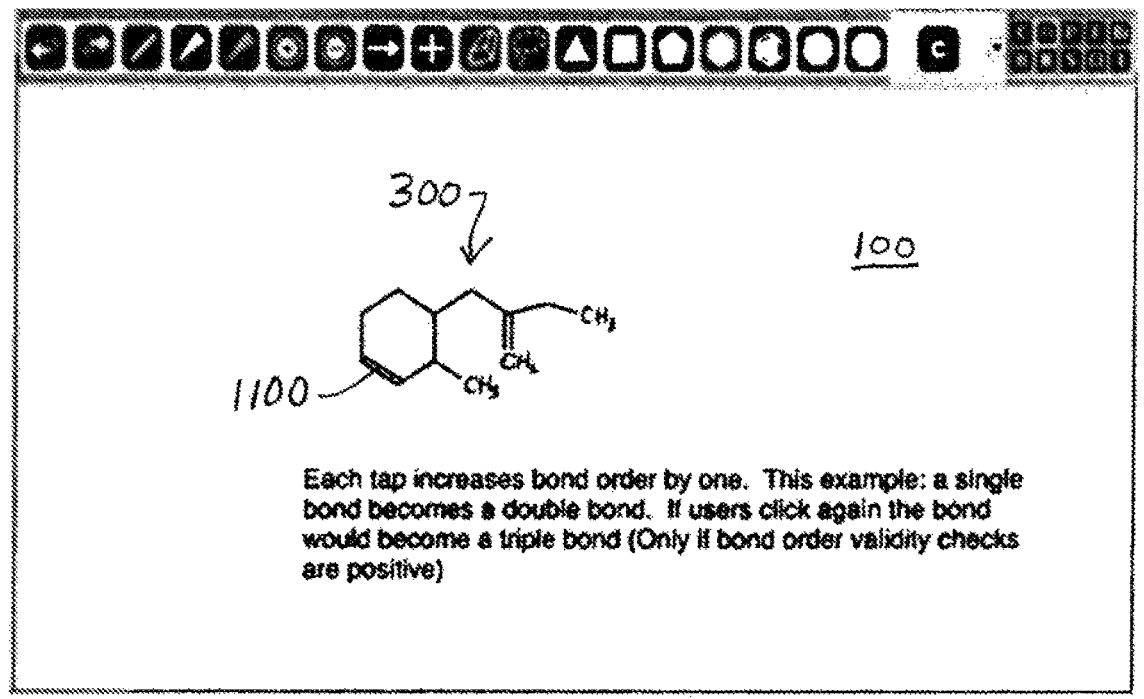

Referring to FIGS. 10 and 11, in some embodiments, the user changes a bond order in the chemical structure representation 300 by performing a bond tap gesture. The user performs the bond tap gesture by tapping the input interface 100 with a finger 1000 in a location corresponding to a chemical bond 1002 in the chemical structure representation 300. With each successive tap on the input interface 100, the order of the bond 1002 is toggled (e.g., increased by one). For example, tapping a representation of a single bond 1002, as shown in FIG. 10, may change the representation to a double bond 1100, as shown in FIG. 11. A further tap may change the representation to a triple bond, or back to a single bond. As mentioned above, the apparatus, systems, and methods may perform a validity check to ensure that each type of bond representation displayed on the graphical display is chemically valid. For example, the user may be prevented from selecting a chemically invalid bond order.

Figure 12:
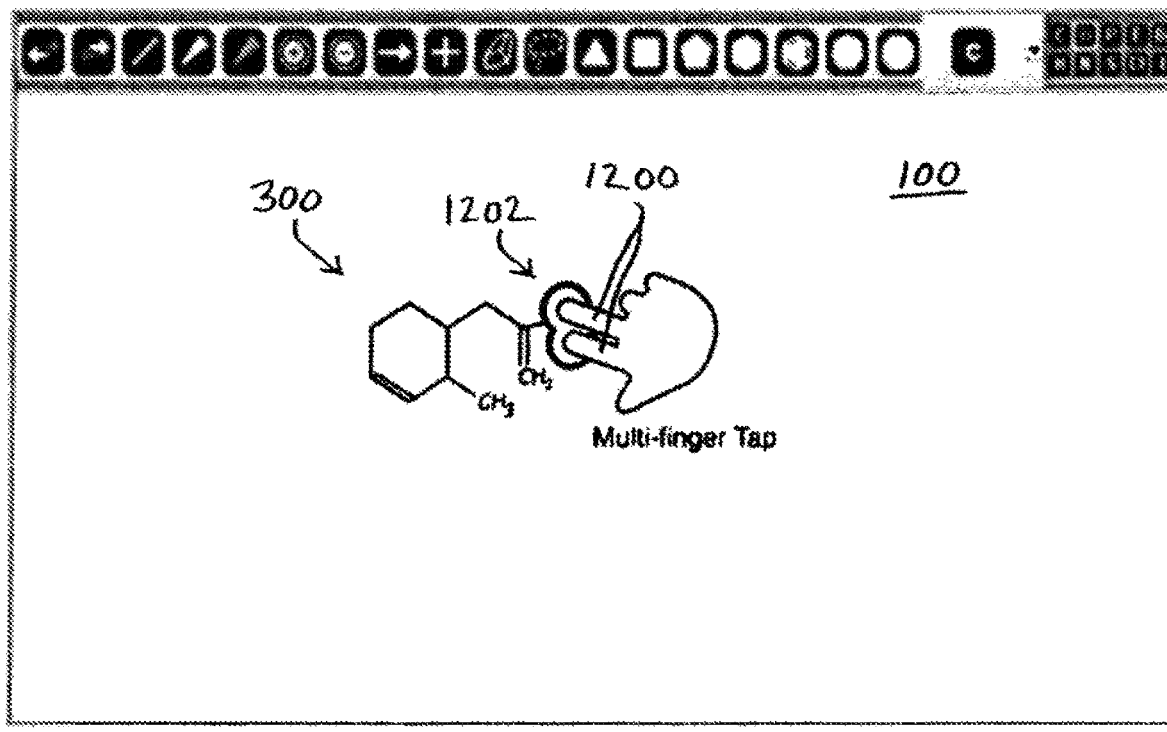
FIG. 12 is a schematic screenshot depicting a two-fingered bond tap gesture for changing a stereo chemical bond assignment, in accordance with an illustrative embodiment of the invention.

Referring to FIG. 12, in various embodiments, the user changes a stereo chemical bond assignment in the chemical structure representation 300 by performing a two-fingered bond tap gesture. The user performs the two-fingered bond tap gesture by tapping the input interface 100 with two (or more) fingers 1200 in a location corresponding to a chemical bond 1202 in the chemical structure representation 300. For example, tapping a representation of a single bond with two fingers may change the bond representation to a wedge bond. A further tap may change the wedge bond representation to a hashed or squiggly bond representation. In one embodiment, with each successive two-fingered tap, the bond representation toggles through a contextual selection of stereochemistry representations. As mentioned, the apparatus, systems, and methods may prevent the user from selecting chemically invalid stereochemistry representations.

Figure 13:
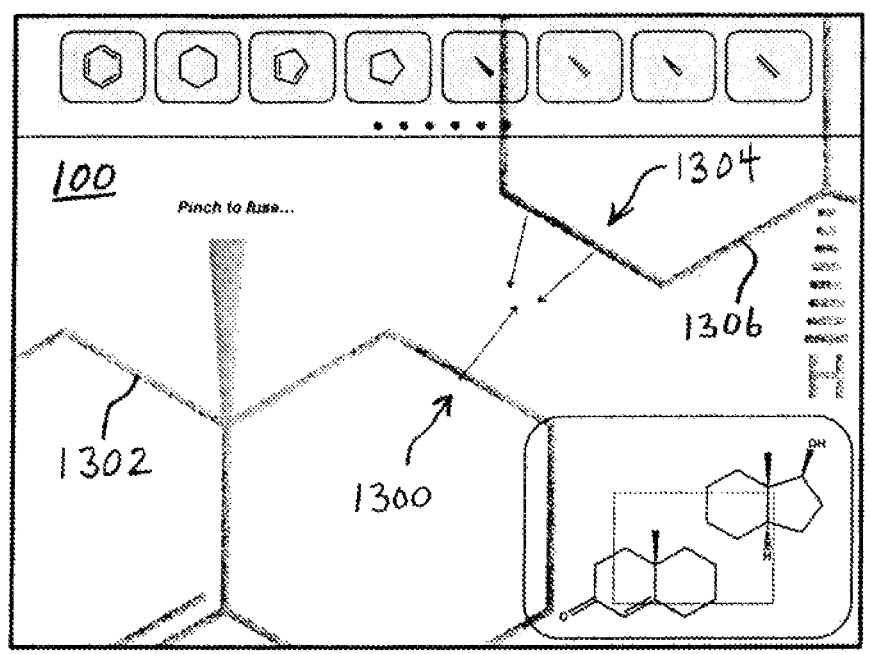
FIGS. 13 and 14 are schematic screenshots depicting a pinch gesture for joining two chemical structure representations, in accordance with an illustrative embodiment of the invention.
Figure 14:
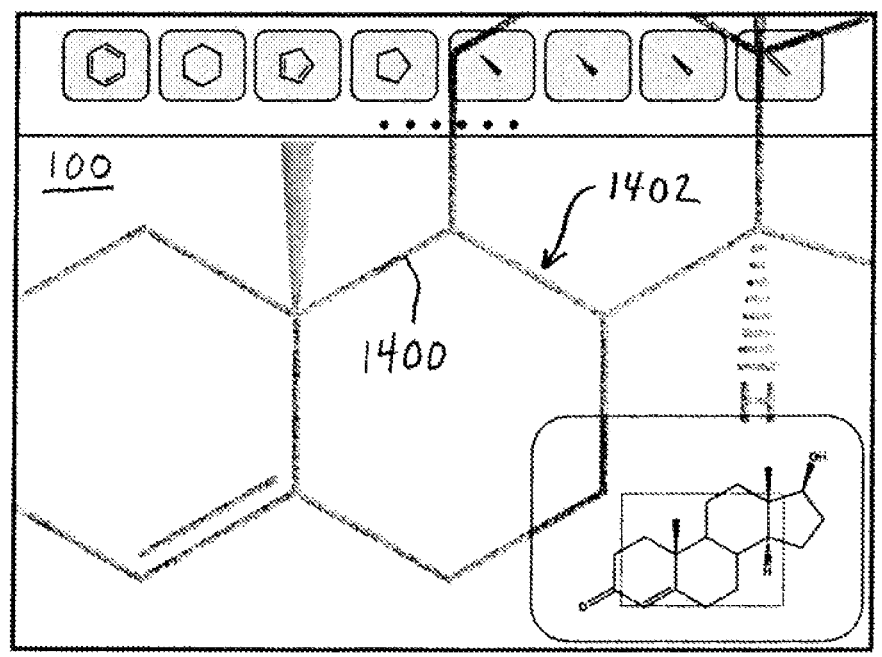

Referring to FIGS. 13 and 14, in certain embodiments, a user joins two chemical structure representations together by performing a pinch gesture. The user performs the pinch gesture by contacting the input interface 100 with a first finger at a first location 1300 corresponding to a first chemical structure representation 1302, and with a second finger at a second location 1304 corresponding to a second chemical structure representation 1306. In one embodiment, the user contacts the first location 1300 and/or the second location 1304 with more than one finger. The user then pinches or drags the first and second fingers together along the input interface 100. Referring to FIG. 14, upon pinching the fingers together, the first and second chemical structure representations 1302, 1306 are snapped or joined together to form a new chemical structure representation 1400. In the depicted embodiment, the user joins the two chemical structure representations 1302, 1306 together at a bond location 1402 by originating the pinch gesture at chemical bonds in the first and second chemical structure representations 1302, 1306. Alternatively, the user may originate the pinch gesture at atomic sites to join the two chemical structure representations 1302, 1306 at an atom location. As mentioned, the user may be prevented from joining the two chemical structure representations 1302, 1306 to produce a chemically invalid structure representation.

Figure 15:
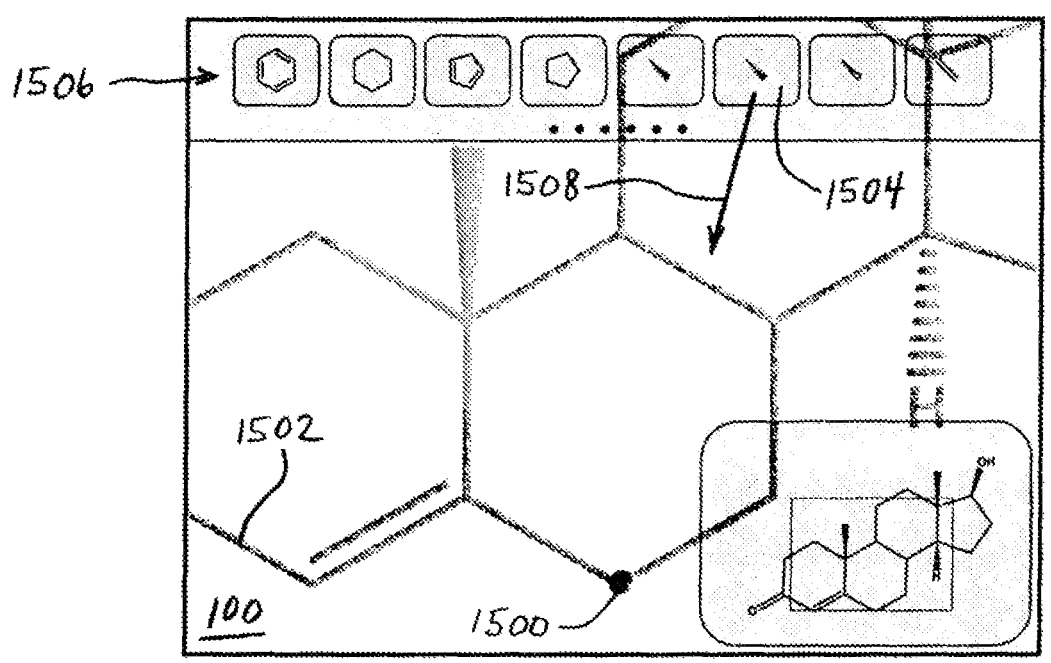
FIG. 15 is a schematic screenshot depicting a fling gesture for joining two chemical structure representations, in accordance with an illustrative embodiment of the invention.

Referring to FIG. 15, in certain embodiments, the user joins two chemical structure representations together by performing a fling gesture. The user performs the fling gesture by tapping or pressing the input interface 100 with a first finger at a first location corresponding to a target 1500 on a chemical structure representation 1502. Once the target 1500 has been selected by tapping or pressing the first location, the user contacts the input interface 100 with a second finger at a second location corresponding to a chemical structure element representation 1504 in a menu 1506. The user then flicks the second finger along the input interface 100 in a direction 1508 corresponding to the target 1500. In one embodiment, the finger is flicked as though the user were attempting to fling or slide the structure element representation 1504 across the graphical display towards the target 1500. In general, to perform the flick, the second finger does not travel an entire distance from the second location to the first location. Instead, the second finger may travel, for example, about half of the entire distance, or less. Upon receiving the flick from the second finger, the structure element representation 1504 may be added to the chemical structure representation 1502 at the target 1500. As mentioned, the apparatus, systems, and methods may prevent addition of the structure element representation 1504 to the chemical structure representation 1502 if the addition is not chemically feasible. In one embodiment, the structure element representation 1504 animates across the graphical display from the menu 1506 to the chemical structure representation 1502, following the flick of the second finger.

Figure 16:
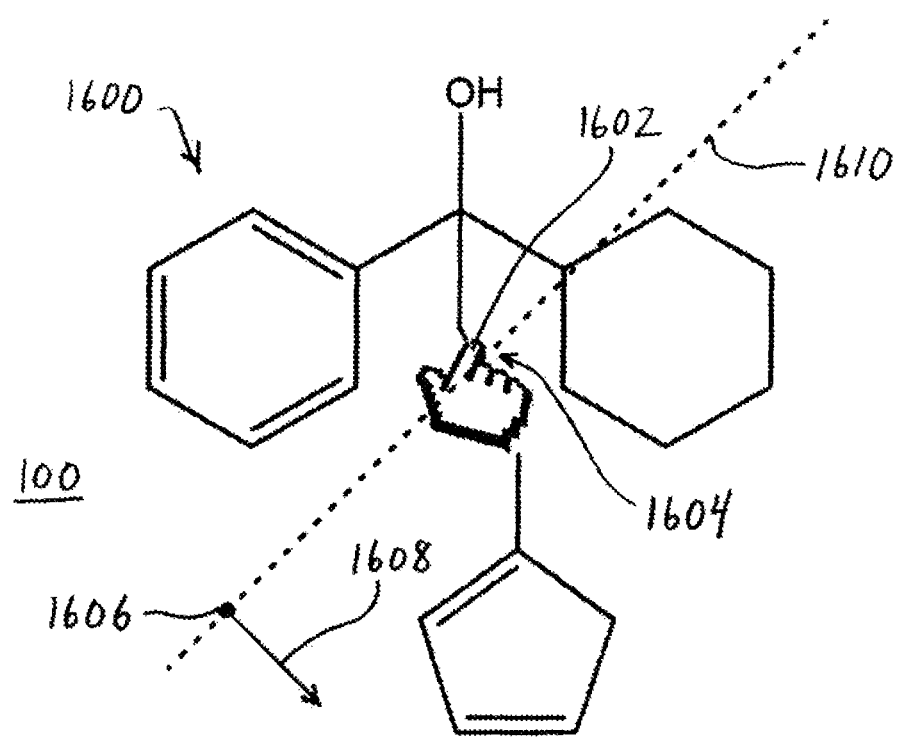
FIG. 16 is a schematic screenshot depicting a flick gesture for rotating a chemical structure representation in a graphical display, in accordance with an illustrative embodiment of the invention.

In the embodiment depicted in FIG. 16, the user rotates a chemical structure representation 1600 by performing a flick gesture. The user performs the flick gesture by tapping and holding a first finger 1602 on the input interface 100 in a first location corresponding to a pivot point 1604 on or near the chemical structure representation 1600. The user then contacts the input interface 100 with a second finger in a second location corresponding to a push point 1606 and flicks the second finger in a flick direction 1608 along the input interface 100. In one embodiment, the flick direction 1608 is substantially orthogonal to a line 1610 between the first location and the second location. Upon receiving the flick from the second finger, the chemical structure representation 1600 rotates about an axis of rotation that passes through the pivot point in a direction perpendicular to the graphical display. In general, the rotation of the chemical structure representation 1600 occurs in the flick direction 1608 at an initial velocity corresponding to a velocity of the flick. In one embodiment, the velocity of rotation of the chemical structure representation 1600 decelerates from the initial velocity to zero over a period of time (e.g., less than about three seconds), following the flick.

Figure 18:
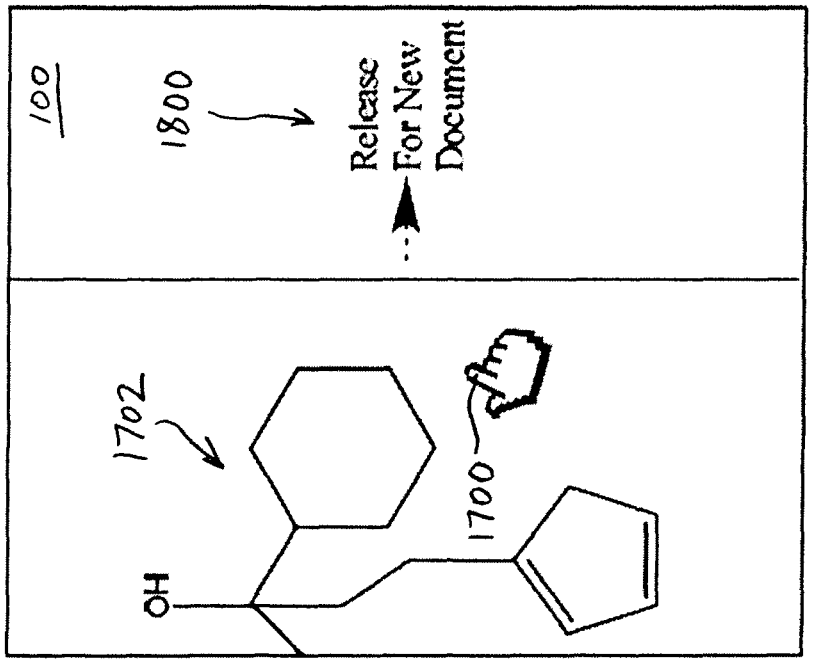
FIGS. 17 and 18 are schematic screenshots depicting a drag gesture for creating an electronic document for a chemical structure representation, in accordance with an illustrative embodiment of the invention.
Figure 17:
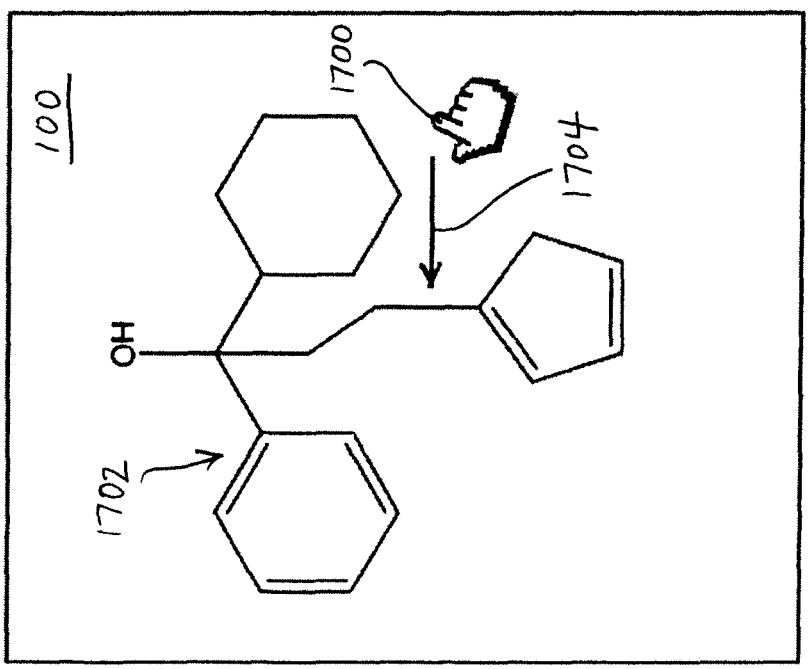

Referring to FIGS. 17 and 18, in certain embodiments, the user creates an electronic document for a chemical structure representation by performing a drag gesture. The user performs the drag gesture by contacting the input interface 100 with a finger 1700 at a location corresponding to empty space around a chemical structure representation 1702. The user then drags the finger 1700 along the input interface 100 in a drag direction 1704, as though the user were attempting to slide the chemical structure representation 1702 to an edge of the graphical display. The drag direction 1704 may be any direction along the graphical display, such as left (as depicted), right, up, or down. Referring to FIG. 18, upon receiving the drag gesture, the chemical structure representation 1702 translates along the graphical display in the drag direction 1704, and an indication 1800 is provided in the graphical display that release of the drag gesture will create a new electronic document. In the depicted embodiment, the indication 1800 is an arrow and a text message stating "Release for New Document." Alternatively, the indication 1800 may include any symbol, text, or combination thereof. The user then removes the finger 1700 from the input interface 100 and the new electronic document is created. The new electronic document may include the chemical structure representation 1702, a portion of the chemical structure representation 1702, a different chemical structure representation (e.g., a template representation), or no chemical structure representation.

In certain embodiments, the apparatus, systems, and methods described herein include a set of chemical cleaning rules for creating and displaying chemical structure representations. In various embodiments, the chemical cleaning rules perform a structure cleanup that includes, for example, normalizing bond lengths, performing global orientation, standardizing ring exterior angles, iteratively normalizing a ring system, performing ring perception (e.g., to distinguish between ring systems and chain systems), generating chain systems and angles, and/or generating ring systems. Ring system generation may include: (i) identifying an arbitrary seed atom; (ii) calculating angular demand of atoms generally using, for example, 180−(360/R), where R is a radius; and (iii) using angular demand to place neighboring atoms in the ring system. In one embodiment, special cases angles for bridged and fusion systems are applied. These structure cleanup methods may be useful to generate diagrams from SMILES, InChi, chemical names, etc. In various embodiments, an interactive method for performing structure cleanup starts with a user-drawn structure. The user may then apply the interactive method multiple times for progressive refinement.

In various embodiments, the user has complete control over a font selection, a font size, and/or a font styling to be used the chemical structure representations. Fonts may utilize or include templates from industry standard journals and organizations. These templates may include specific font styles, font sizes, bond lengths, and/or bond widths. In one embodiment, an important aspect of font handling is bond-truncation. For example, bonds that join text may be treated specially, glyphs may be converted to bitmaps and analyzed, and bonds may be truncated according to a standard distance from a glyph using a radial search of a bitmap.

In certain embodiments, bonds are drawn as 6-membered polygons. Wedges may be mitered according to a glyph using a bond truncation algorithm.

Figure 19:
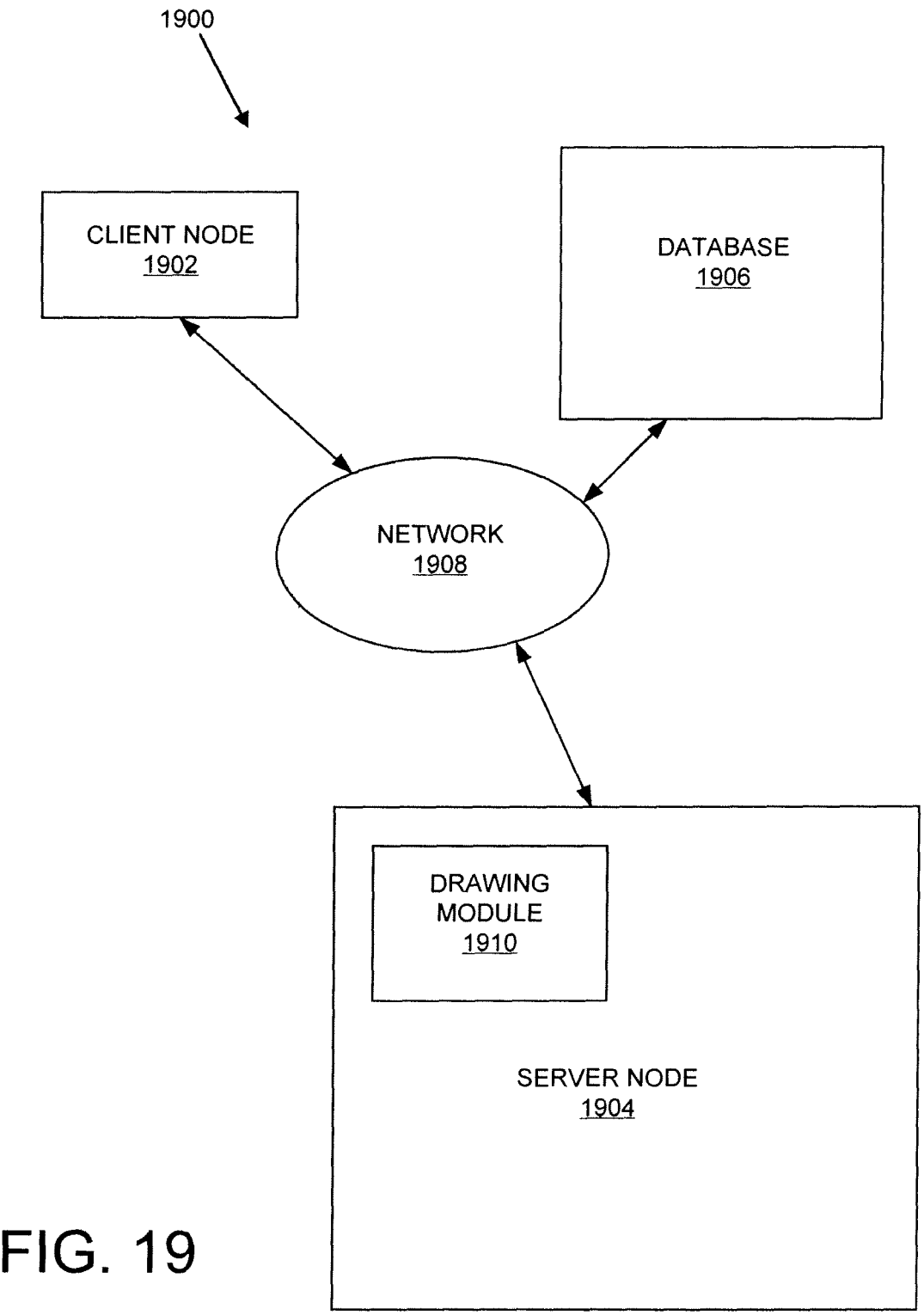
FIG. 19 is a schematic diagram of a system for drawing or editing chemical structures, in accordance with an illustrative embodiment of the invention.

FIG. 19 depicts a system 1900, according to an illustrative embodiment of the invention, for drawing or editing chemical structures. The system 1900 includes a client node 1902, a server node 1904, a database 1906, and, for enabling communications therebetween, a network 1908. As illustrated, the server node 1904 may include a drawing module 1910.

The network 1908 may be, for example, a local-area network (LAN), such as a company or laboratory Intranet, a metropolitan area network (MAN), or a wide area network (WAN), such as the Internet. Each of the client node 1902, server node 1904, and the database 1906 may be connected to the network 1908 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 1902 may be any type of personal computer, Windows-based terminal, network computer, wireless device, information appliance, RISC Power PC, X-device, workstation, mini computer, main frame computer, tablet computer, personal digital assistant, set top box, cellular phone, handheld device, or other computing device that is capable of both presenting information/data to, and receiving commands from, a user of the client node 1902 (e.g., an analytical chemist). The client node 1902 may include, for example, a graphical display device (e.g., a touch screen or a computer monitor), a data entry device (e.g., a keyboard, a touch screen, or a mouse pad), persistent and/or volatile storage (e.g., computer memory), a processor, and a mouse. In one embodiment, the client node 1902 includes a web browser, such as, for example, the INTERNET EXPLORER program developed by Microsoft Corporation of Redmond, Wash., to connect to the World Wide Web.

For its part, the server node 1904 may be any computing device that is capable of receiving information/data from and delivering information/data to the client node 1902, for example over the network 1908, and that is capable of querying, receiving information/data from, and delivering information/data to the server node 1904. For example, as further explained below, the server node 1904 may receive input (e.g., a multi-touch gesture) from a user of the client node 1902, create or edit a chemical structure representation according to the input, and present or display the chemical structure representation to the user at the client node 1902. The server node 1904 may include a processor and persistent and/or volatile storage, such as computer memory.

The server node 1904 may be any computing device that is capable of storing and managing collections of data, such as data relating to chemical structure representations. The chemical structure representations may be, for example, of the type described in co-pending U.S. patent application Ser. No. 13/100,217, filed May 3, 2011, titled "Systems, Methods, and Apparatus for Processing Documents to Identify Structures," and co-pending U.S. application Ser. No. 13/239,069, filed, Sep. 21, 2011, titled "Systems, Methods, and Apparatus for Facilitating Chemical Analyses," the disclosures of which are hereby incorporated by reference herein in their entireties.

As used herein, the term "server node" is broadly used to refer to any repository of information. The data stored within the server node 1904 may be harvested from the server node 1904 in any manner. In one embodiment, the harvesting is performed utilizing indexing and structure recognition algorithms, and the harvested data is connected together by examining and correlating the disjointed information that is found.

The drawing module 1910 of the server node 1904 may be implemented as any software program and/or hardware device, for example an application specific integrated circuit (ASIC) or a field programmable gate array (FPGA), that is capable of providing the functionality described herein. It will be understood by one having ordinary skill in the art, however, that the illustrated module 1910, and the organization of the server node 1904, are conceptual, rather than explicit, requirements. For example, it should be understood that the drawing module 1910 may in fact be implemented as multiple modules, such that the functions performed by the single module, as described herein, are in fact performed by the multiple modules.

Although not shown in FIG. 19, each of the client node 1902, the server node 1904, and the database 1906 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 19 is a simplified illustration of the system 1900 and that it is depicted as such to facilitate the explanation of the present invention's embodiments. Moreover, the system 1900 may be modified in a variety of manners without departing from the spirit and scope of the invention. For example, rather than being implemented on a single server node 1904, the drawing module 1910 may instead be implemented on a different computing device (not shown) and such computing devices may communicate with one another directly, over the network 1908, or over another additional network (not shown). In yet another example, the functionality of the server node 1904 may in fact be resident on the server node 1904 (e.g., be implemented in the computer memory thereof). Additional options are for the server node 1904 and/or the database 1906 to be local to the client node 1902 (such that they may all communicate directly without using the network 1908), or for the functionality of the server node 1904 and/or the database 1906 to be implemented on the client node 1902 (e.g., for the drawing module 1910 and/or the server node 1904 to reside on the client node 1902). As such, the depiction of the system 1900 in FIG. 19 is non-limiting.

In certain embodiments, the system 1900 allows a user to draw and edit a chemical structure representation using one or more fingers on an input interface, such as a touch pad or touch screen, at the client node 1902. In general, the drawing module 1910 in the server node 1904 is configured to draw or revise the chemical structure representation according to the input from the user, as explained above with respect to FIGS. 1-18. The drawing module 1910 may then provide an image (e.g., a collection of pixels) of the chemical structure representation for presentation to the user on the graphical display of the client node 1902. In general, the system 1900 may be used to perform any of the methods described herein.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A computer-implemented method comprising:
generating a graphical user interface comprising one or more chemical structure representations, each representation comprising one or more structure elements of a respective chemical structure;
receiving a plurality of signals that are generated responsive to: a user tap gesture detected via a touch-sensitive device at a first location, and a user fling gesture detected via the touch-sensitive device at a second location and proceeding in a direction towards the first location,
wherein the first location corresponds to a first structure element of a first chemical structure representation of the one or more chemical structure representations, and
wherein the second location corresponds to a second structure element of either:
(1) the first chemical structure representation of the one or more chemical structure representations,
(2) a second chemical structure representation of the one or more chemical structure representations, or
(3) a representation of a structure element selected from a menu identifying a plurality of structure elements; and
upon receiving the plurality of signals that are generated responsive to the user tap gesture and the user fling gesture, joining the first structure element and the second structure element in a vicinity of the first structure element and the second structure element to produce a third chemical structure representation.

2. The method of claim 1, wherein the first and second structure elements comprise at least one of an atom and a bond.

3. The method of claim 1, wherein joining in the vicinity of the first and second structure elements to produce the third chemical structure representation further comprises:
joining the first chemical structure representation and the second chemical structure representation, according to a set of chemical structure rules.

4. The method of claim 1, wherein joining in the vicinity of the first and second structure elements to produce the third chemical structure representation further comprises:
joining the representation of the structure element selected from the menu to the structure element at the first location, according to a set of chemical structure rules.

5. The method of claim 1, wherein the joining comprises animating the representation of the structure element selected from the menu, from the second location to the first location on the graphical user interface, in response to the plurality of signals that are generated responsive to the user fling gesture.

6. The method of claim 1, wherein the user tap gesture comprises a tap and hold gesture.

7. The method of claim 1, further comprising:
receiving one or more signals that are generated responsive to a user drag gesture detected by the touch-sensitive device at a location corresponding to empty space around one of the one or more chemical structure representations, wherein the one or more chemical structure representations includes the third chemical structure representation;
upon receiving the one or more signals that are generated responsive to the user drag gesture,
(A) translating the one of the one or more chemical structure representations in a direction corresponding to the drag gesture, and
(B) providing an indication on the graphical user interface that release of the drag gesture will create a new electronic document for the one of the one or more chemical structure representations;
receiving one or more signals that are generated responsive to a release of the drag gesture detected by the touch-sensitive device; and
upon receiving the one or more signals that are generated responsive to the release of the drag gesture, creating the new electronic document.

8. The method of claim 7, wherein the new electronic document displays the one of the one or more chemical structure representations.

9. The method of claim 1, further comprising:
receiving a plurality of signals generated responsive to
a user pinch gesture detected by the touch-sensitive device, wherein the pinch gesture originates at a third location and a fourth location,
wherein the third location corresponds to a third structure element corresponding to one of the one or more chemical structure representations,
wherein the one or more chemical structure representations includes the third chemical structure representation, and
wherein the fourth location corresponds to a fourth structure element corresponding to either:
(1) the one of the one or more chemical structure representations, or
(2) another one of the one or more chemical structure representations, or
(3) a representation of another structure element selected from the menu identifying the plurality of structure elements; and
upon receiving the plurality of signals that are generated responsive to the user pinch gesture, joining the third structure element and the fourth structure element in the vicinity of the third structure element and the fourth structure element to produce a fourth chemical structure representation.

10. A system comprising
one or more processors; and
memory storing computer-executable instructions that, when executed by the one or more processors, cause the system to:
generate a graphical user interface comprising one or more chemical structure representations, each representation comprising one or more structure elements of a respective chemical structure;
receive a plurality of signals that are generated responsive to: a user tap gesture detected via a touch-sensitive device at a first location, and a user fling gesture detected via the touch-sensitive device at a second location and proceeding in a direction towards the first location,
wherein the first location corresponds to a first structure element of a first chemical structure representation of the one or more chemical structure representations, and
wherein the second location corresponds to a second structure element of either:

(1) the first chemical structure representation of the one or more chemical structure representations,
(2) a second chemical structure representation of the one or more chemical structure representations, or
(3) a representation of a structure element selected from a menu identifying a plurality of structure elements; and upon receiving the plurality of signals that are generated responsive to the user tap gesture and the user fling gesture, join the first structure element and the second structure element in a vicinity of the first structure element and the second structure element to produce a third chemical structure representation.

11. The system of claim 10, the memory storing additional computer-executable instructions, which when executed by the one or more processors, cause the system to:
receive a plurality of signals generated responsive to a user pinch gesture originating at a third location and a fourth location
wherein the third location corresponds to a third structure element corresponding to one of the one or more chemical structure representations,
wherein the one or more chemical structure representations includes the third chemical structure representation, and
wherein the fourth location corresponds to a fourth structure element corresponding to either:
(1) the one of the one or more chemical structure representations, or
(2) another one of the one or more chemical structure representations, or
(3) a representation of another structure element selected from the menu identifying the plurality of structure elements; and
upon receiving the plurality of signals that are generated responsive to the user pinch gesture, join the third structure element and the fourth structure element in a vicinity of the third structure element and the fourth structure element to produce a fourth chemical structure representation.

12. The system of claim 10, wherein the first and second structure elements comprise at least one of an atom and a bond.

13. The system of claim 10, wherein joining in the vicinity of the first and second structure elements to produce the third chemical structure representation further comprises:
joining the first chemical structure representation and the second chemical structure representation, according to a set of chemical structure rules.

14. The system of claim 10, wherein joining in the vicinity of the first and second structure elements to produce the third chemical structure representation further comprises:
joining the representation of the structure element selected from the menu to the structure element at the first location, according to a set of chemical structure rules.

15. The system of claim 10, wherein the joining comprises animating the representation of the structure element selected from the menu, from the second location to the first location on the graphical user interface, in response to the plurality of signals that are generated responsive to the user fling gesture.

16. The system of claim 10, wherein the user tap gesture comprises a tap and hold gesture.

17. The system of claim 10, the memory storing additional computer-executable instructions, which when executed by the one or more processors, cause the system to:
receive one or more signals that are generated responsive to a user drag gesture detected by the touch-sensitive device at a location corresponding to empty space around one of the one or more chemical structure representations, wherein the one or more chemical structure representations includes the third chemical structure representation;
upon receiving the one or more signals that are generated responsive to the user drag gesture,
(A) translate the one of the one or more chemical structure representations in a direction corresponding to the drag gesture, and
(B) provide an indication on the graphical user interface that release of the drag gesture will create a new electronic document for the one of the one or more chemical structure representations;
receive one or more signals that are generated responsive to a release of the drag gesture delivered upon the touch-sensitive device; and
upon receiving the one or more signals that are generated responsive to the release of the drag gesture, create the new electronic document.

18. One or more non-transitory computer readable media storing computer-executable instructions that, when executed, cause a computing device to:
generate a graphical user interface comprising one or more chemical structure representations, each representation comprising structure elements of a respective chemical structure;
receive a plurality of signals that are generated responsive to: a user tap gesture detected via a touch-sensitive device at a first location, and a user fling gesture detected via the touch-sensitive device at a second location and proceeding in a direction towards the first location,
wherein the first location corresponds to a first structure element of a first chemical structure representation of the one or more chemical structure representations, and
wherein the second location corresponds to a second structure element of either:
(1) the first chemical structure representation of the one or more chemical structure representations,
(2) a second chemical structure representation of the one or more chemical structure representations, or
(3) a representation of a structure element selected from a menu identifying a plurality of structure elements; and
upon receiving the plurality of signals that are generated responsive to the user tap gesture and the user fling gesture, join the first structure element and the second structure element in a vicinity of the first structure element and the second structure element to produce a third chemical structure representation.

* * * * *